US007358417B2

(12) United States Patent
Song et al.

(10) Patent No.: US 7,358,417 B2
(45) Date of Patent: Apr. 15, 2008

(54) TRANSGENIC ORGANISM EXPRESSING FUNGAL MRP-LIKE ABC TRANSPORTERS

(75) Inventors: Won Yong Song, Kyungsangbuk-do (KR); Young Yeul Yang, Kyungki-do (KR); YoungSook Lee, Kyungsangbuk-do (KR); InWhan Hwang, Pohang (KR); Eun Woon Noh, Kyungki-do (KR); Young Im Choi, Kyungki-do (KR); Eun Hwa Jeong, Kyungsangbuk-do (KR); Enrico Martinoia, Zurich (CH)

(73) Assignees: POSCO (KR); POSTECH Foundation (KR)

( * ) Notice: Subject to any disclaimer, the term of this patent is extended or adjusted under 35 U.S.C. 154(b) by 121 days.

(21) Appl. No.: 10/492,880

(22) PCT Filed: Oct. 16, 2002

(86) PCT No.: PCT/KR02/01934

§ 371 (c)(1),
(2), (4) Date: Nov. 9, 2004

(87) PCT Pub. No.: WO03/033705

PCT Pub. Date: Apr. 24, 2003

(65) Prior Publication Data

US 2005/0091709 A1 Apr. 28, 2005

(30) Foreign Application Priority Data

Oct. 16, 2001 (KR) .............................. 2001/63802
Oct. 15, 2002 (KR) .............................. 2002/62984

(51) Int. Cl.
*A01H 5/00* (2006.01)
*C12N 15/09* (2006.01)
*C12N 15/82* (2006.01)

(52) U.S. Cl. ................. 800/278; 800/298; 800/295; 800/306; 435/69.1; 435/468

(58) Field of Classification Search ................ 800/278, 800/298, 295, 288; 435/320.1, 69.1, 468; 536/23.7, 23.2
See application file for complete search history.

(56) References Cited

U.S. PATENT DOCUMENTS

| 5,624,711 | A | 4/1997 | Sundberg et al. |
| 5,888,981 | A | 3/1999 | Bujard et al. |
| 6,001,553 | A | 12/1999 | Broach et al. |
| 6,100,042 | A | 8/2000 | Fowlkes et al. |
| 6,166,290 | A * | 12/2000 | Rea et al. ................. 800/278 |
| 6,242,667 | B1 | 6/2001 | Bujard et al. |
| 6,252,136 | B1 | 6/2001 | Bujard et al. |
| 6,410,041 | B1 | 6/2002 | Lewis et al. |

FOREIGN PATENT DOCUMENTS

WO    WO 0029373    5/2000

OTHER PUBLICATIONS

Szczypka et al. J. Biol. Chem.(1994), vol, 269 (36), pp. 22853-22857.*
Salt et al. Biotechnology, vol. 13, pp. 468-474, 1995.*
Guerinot et al (Plant Physiology (2001), vol. 125, pp. 164-167.*
Peter Goldsbrough ((1999), Ann Arbor Press, pp. 221-228, 1999.*
Arazi et al. The Plant Journal (1999) 20 (2), pp. 171-182.*
Klein, M., et al. (2002) "The ATP-Binding Cassette (ABC) Transporter Bpt1p Mediates Vacuolar Sequestration of Glutathione Conjugates in Yeast." FEBS Lett., 520, 63-67.
Sharma KG et al. (2002) "Localization, regulation, and substrate transport properties of Bpt1p, a *Saccharomyces cerevisiae* MRP-type ABC transporter." Eukaryot Cell. Jun;1(3):391-400.
Dominguez-Solis, JR et al. (2001) "The cytosolic O-acetylserine(thiol)lyase gene is regulated by heavy metals and can function in cadmium tolerance." J Biol Chem vol. 276, p. 9297.
Mejare M, Bulow L., (2001) "Metal-binding proteins and peptides in bioremediation and phytoremediation of heavy metals" , Trends Biotechnol. Feb;19(2):67-73.
Hirschi K. et al. (2000). "Expression of *Arabidopsis* CAX2 in Tobacco: Altered Metal Accumulation and Increased Manganese Tolerance." Plant Physiol 124: 125-134.
Petrovic S. et al. (2000) "The products of YCF1 and YLL015w (BPT1) cooperate for the ATP-dependent vacuolar transport of unconjugated bilirubin in *Saccharomyces cerevisiae*."; Yeast 16:561-571.
Beier et al. (1999) "Versatile derivatisation of solid support media for covalent bonding on DNA-microchips", Nucleic Acids Research 27: 1970-1977.
Falcon-Perez JM, et al. (1999) "Functional domain analysis of the yeast ABC transporter Ycf1p by site-directed mutagenesis." J Biol Chem. Aug. 13;274(33):23584-90.
Ghosh M. et al. (1999) "Pathways of As(III) detoxification in *Saccharomyces cerevisiae*." Proc Natl Acad Sci USA 96: 5001-5006.
Slomkowski et al. (1999) "Inorganic-organic systems with tailored properties controlled on molecular, macromolecular and microscopic level", Reactive & Functional Polymers 41: 45-57.
Zhu YL et al., (1999) "Overexpression of glutathione synthetase in Indian mustard enhances cadmium accumulation and tolerance." Plant Physiol 119: 73-79.
Clough S.J. et al., (1998) "Floral dip: a simplified method for Agrobacterium-mediated transformation of *Arabidopsis thaliana*." Plant J 16:735-43.

(Continued)

*Primary Examiner*—Medina A. Ibrahim
(74) *Attorney, Agent, or Firm*—Baker Botts LLP

(57) ABSTRACT

The invention relates to a transgenic plant or yeast comprising a DNA molecule encoding fungal ATP-binding cassette (ABC) transporter protein, which confers resistance to, and/or accumulation of heavy metals and herbicides. The invention also relates to methods of producing transgenic plants expressing fungal YHL035C protein, which can be used for removing heavy metals and herbicides from polluted soil or water.

6 Claims, 11 Drawing Sheets

OTHER PUBLICATIONS

Decottignies A. et al. (1998) "ATPase and multidrug transport activities of the overexpressed yeast ABC protein Yor1p." J Biol Chem. May 15;273(20):12612-22.

Lanphear, B.P. (1998) The paradox of lead poisoning prevention. Science. 281; 1617-1618.

Rensing, C., Sun, Y., Mitra, B., and Rosen, B.P. (1998) Pb (II)-translocating P-type ATPases. J. Biol. Chem. 273: 32614-32617.

Salt DE, Smith RD, Raskin I (1998). Phytoremediation. Annual Review of Plant Physiology and Plant Molecular Biology 49: 643-668.

Tsubokawa et al. (1998) "Grafting of 'dendrimer-like' highly branched polymer onto ultrafine silica surface", Reactive & Functional Polymers 37: 75-82.

Li, ZS et al., (1997) "A new pathway for vacuolar cadmium sequestration in *Saccharomyces cerevisiae* : YCF1-CATALYZED transport of bis (GLUTATHIONATO) cadmium." Proc. Natl. Acad. Sci. USA 94,42-47.

Ortiz DF et al. (1997) "A yeast ATP-binding cassette-type protein mediating ATP-dependent bile acid transport." J Biol Chem. Jun. 13;272(24):15358-65.

Li ZS et al. (1996) "The Yeast Cadmium Factor Protein (YCF1) Is a Vacuolar Glutathione S-Conjugate Pump" J. Biol. Chem., Mar. 15,; 271(11): 6509-6517.

Lloyd, G. and McCown, B.H. 1981. "Commercially feasible micropropagation of mountain laurel (*Kalmia latiflora*) by use of shoot tip culture." Proc. Int. Plant Prop. Soc. 30:421-427.

Murashige, T. and F. Skoog. 1962. "A revised medium for rapid growth and bioassays with tobacco tissue cultures." Physiol. Plant. 15:473-497.

VMR1/YHL035C Summary., printed Jan. 23, 2006.

Decottignies A, Goffeau A. Complete inventory of the yeast ABC proteins. Nat Genet. Feb. 1997;15(2):137-45.

Grec S et al: "Cryptic polyadenylation sites within the coding sequence of three yeast genes expressed in tobacco" Gene, Elsevier Biomedical Press. Amsterdam, NL, vol, 242, No. 1-2, Jan. 2000, pp. 87-95, XP004196507.

Database Swissprot Probable ATP-dependent permease YHL035C, Feb. 1, 1995, XP002331356.

Bauer B E et al: Inventory and function of yeast ABC proteins: about sex, stress, pleiotropic drug and heavy metal resistance: Biochimica et Biophysica Acta. Biomembranes, Amsterdam, NL, vol. 1461, No. 2, Dec. 6, 1999, pp. 217-236, XP004273094.

* cited by examiner

C 1.8 mM Pb

US 7,358,417 B2

TRANSGENIC ORGANISM EXPRESSING FUNGAL MRP-LIKE ABC TRANSPORTERS

CROSS REFERENCE TO RELATED APPLICATION

This application is based on Korean Patent Application Nos. 2001-0063802 and 2002-0062984 filed with Korean Intellectual Property Office on Oct. 16, 2001 and Oct. 15, 2002, respectively.

BACKGROUND OF THE INVENTION (a) Field of the Invention

The present invention relates to a fungal MRP-like ABC transporter gene and organisms transformed with the gene, and more particularly, to transformed organisms expressing fungal MRP-like ABC transporter genes Including YCF1 or YHL035C, and thereby having improved resistance to and accumulation of toxic materials such as lead, cadmium, arsenic, and herbicides.

(b) Description of the Related Art

Heavy metals such as lead, cadmium, mercury and so on accumulate in the human body through nature's food chain and cause chronic damage to the brain, nerves, bones, etc., and the polluted environment and damage continues from generation to generation. Typical examples of problems caused by heavy metal toxicity are Minamata disease and Itaiitai disease, which have occurred in Japan. As lead is a pollutant that causes the most damage among the heavy metals (Salt, D. E., Smith, R. D., and Raskin, I. Phytoremediation. *Annu. Rev. Plant Physiol. Plant Mol. Biol.* 49, 643-668 (1998)), it is very important to rid lead from the environment. The United States government expends approximately 500 million dollars each year in order to remove lead from environments where children are raised (Lanphear, B. P. The paradox of lead poisoning prevention. *Science.* 281; 1617-1618 (1998)). Additionally, as arsenic pollutes drinking water and causes skin diseases and cancer, it is becoming a serious problem.

As known genes associated with resistance to or accumulation of toxic materials such as heavy metals and agricultural chemicals, bacterial P-type ATPase has a role in pumping lead to outside of cells at bacterial cell membranes (Rensing, C., Sun, Y., Mitra, B., and Rosen, B. P. Pb(II)-translocating P-type ATPases. *J. Biol. Chem.* 273: 32614-32617 (1998)); genes associated with cadmium resistance include the YCF1 gene of yeast; and genes associated with resistance to arsenic include the YCF1 and ACR genes of yeast, ArsAB of bacteria, etc.

Living organisms have a mechanism for mitigating toxicity of materials using transporter proteins or biological materials having affinity for noxious materials that invade the body. Use of genes contributing to living organism's resistance against noxious materials would provide an environmentally-friendly way to remediate environments polluted with noxious materials at a very low cost as compared with the physical and/or chemical remediation that is currently widely being employed (Mejare and Bulow, Trends in Biotechnology; 2001, Raskin I. and Ensley B. D. Phytoremediaton of Toxic Metals., John Wily & Sons, New York; 2000). In particular, as plants have many advantages such as their ability to express foreign genes readily and thus exhibit new phenotypes, they can be produced and maintained at a low cost, they are aesthetically pleasing, etc., research on improvement of plants by inserting useful genes thereinto for use in environmental remediation is being actively conducted. This technique, the use of plants for cleaning up environment, is called "Phytoremediation."

Under the circumstance where environmental pollution in soil, etc. due to toxic materials such as lead, cadmium, arsenic, and agricultural chemicals is serious, there is a great need for organisms that are transformed by genes that confer resistance to and/or accumulation of these toxic materials.

Transformed plants that can be used to remove cadmium from the environment have been disclosed in several papers (Zhu et al., (1999) *Plant Physiol.* 119: 73-79, Hirschi et al., (2000) *Plant Physiol.* 124:125-33, Dominguez-Solis et al., (2001) *J. Biol. Chem.* 276: 9297-9302), but there have been no report of transgenic plants that are enhanced in the capacity to remove lead or arsenic from the environment. Further, attempts to develop organisms transformed with YCF1 to improve resistance to not only lead but also to cadmium, arsenic, and herbicides for removal of these toxic materials have not yet been disclosed.

SUMMARY OF THE INVENTION

The present invention relates to a DNA molecule exhibiting resistance to and accumulation of lead, and encoding fungal MRP-like ABC transporter protein (multidrug resistance-associated protein ATP-binding cassette transporter protein, MRP-like ABC transporter protein).

Further, the invention relates to a recombinant vector comprising said DNA molecule encoding MRP-like ABC transporter protein.

Still further, the invention relates to transformed organisms with improved resistance to and/or accumulation of toxic materials, which are transformed with said DNA molecule encoding fungal MRP-like ABC transporter protein.

DETAILED DESCRIPTION AND THE PREFERRED EMBODIMENTS

Figure 1:
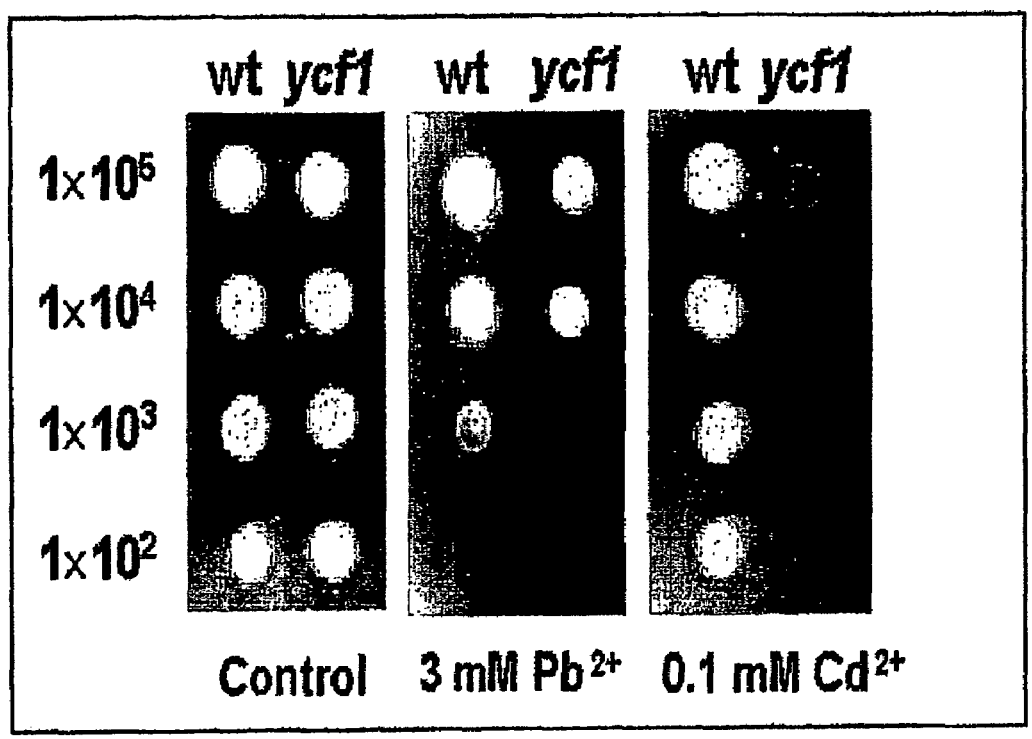
FIG. 1 shows photographs of wild type and YCF1 null (ycf1) yeasts growing on control, lead or cadmium-containing media, and shows that the ycf1 mutant yeast is more sensitive to lead and cadmium than wild type yeast.

The present invention relates to a gene exhibiting resistance to and/or accumulation of toxic materials, a vector comprising the gene, and cells and organisms transformed therewith.

The gene exhibiting resistance to and/or accumulation of toxic materials in the present invention is a gene encoding fungal multidrug resistance associated protein (MRP)-like ATP-binding cassette transporter protein (hereinafter referred to as "MRP-like ABC transporter protein").

The fungal MRP-like ABC transporter protein, which is a kind of ABC transporter protein, has a role in transporting several organic materials present in cytoplasm to the outside of the cytoplasm. ABC transporter proteins exist in several organisms ranging from prokaryotic organisms to human liver cells, and they transport a large variety of materials. Organic materials transported by the ABC transporter proteins include heavy metals conjugated with glutathione, bile acids, etc. YCF1 belonging to the fungal MRP-like ABC transporter proteins is known to transport cadmium, arsenic, and agricultural chemicals into vacuoles and thereby confer resistance to these noxious materials (Li et al., (1997) *Proc. Natl. Acad. Sci. USA* 94: 42-47, Ghosh et al., (1999) *Proc. Natl. Acad. Sci. USA* 96: 5001-5006). However, an attempt to develop organisms with improved resistance to all of cadmium, arsenic, and agricultural chemicals using YCF1 for removal of noxious materials has not yet been disclosed. Furthermore, the contribution of YCF1 to resistance to lead has not yet been reported, and there has been no disclosure regarding the function of YHL035C protein and transformants expressing It.

The fungal MRP-like ABC transporter genes include, as examples, YCF1 (Yeast cadmium factor 1) and YHL035C genes, and MRP-like ABC transporter genes having at least 28% sequence homology in amino acid sequence with YCF1 protein and YHL035C protein. YCF1 and YHL035C genes, or their proteins, have 28% sequence homology with each other. Also, this Invention is Intended to include DNA molecules encoding fungal MRP-like ABC transporter proteins and having at least 28% sequence homology, preferably at least 40% homology, and more preferably at least 50% homology in amino acid sequence with YCF1 or YHL035C protein. For example, BPT1, YBT1, and YOR1 genes, which have at least 28% homology In amino acid sequence with YCF1 or YHL035C proteins, can be included from a comparison conducted in the amino acid database from the GenBank using the CLUSTRALW program. The BPT1 protein has 40% homology In amino acid sequence with YCF1, YBT1 protein has 51% homology in amino acid sequence with YHL035C, and YOR1 protein has 28% homology in arnino acid sequence with YCF1. YBT1 and BPT1 are fungal MRP-like ABC transporter proteins that are known to transport bile acids (Ortiz et al., (1997) *Journal of Biological Chemistry* 272: 15358-15365, Petrovic et al., (2000) *Yeast* 16: 561-571), and YOR1 protein, also a fungal MRP-like ABC transporter protein, has been known to transport several drugs (Decottignies et al., (1998) *Journal of Biological Chemistry* 273: 12612-12622).

The MRP-like ABC transporter proteins according to the present invention have been known to have a common domain structure, comprising an N-terminal extension domain, which is a considerably lengthy and hydrophbic domain at the N-terminal; a first transmembrane spanning domain; a first nucleotide binding fold domain, which is a cytoplasmic domain; a second transmembrane spanning domain; and a second nucleotide binding fold domain, which is a cytoplasmic domain located at the C-terminal.

In a preferred embodiment of the invention, the fungal MRP-like ABC transporter proteins have a sequence homology of at least 28%, preferably at least 40%, and more preferably at least 50%, with the amino acid sequence of YCF1 protein of SEQ ID NO:2 or YHL035C protein of SEQ ID NO:4, each of which comprises an N-terminal extension domain, a first transmembrane spanning domain, a first nucleotide binding fold domain, a second transmembrane spanning domain, and a second nucleotide binding fold domain, and each domain of the fungal MRP-like ABC transporter proteins may have at least 28% sequence homology with the amino acid sequence of each corresponding domain of YCF1 protein of SEQ ID NO:2 or YHL035C protein of SEQ ID NO:4.

The gene conferring both resistance to and accumulation of toxic materials in the present invention is a YCF1 gene comprising a sequence encoding the polypeptide of YCF1 protein, for example, a nucleotide sequence encoding the polypeptide of SEQ ID NO:2 exhibiting resistance to noxious materials and accumulation of noxious materials; preferably a YCF1 gene exhibiting resistance to or accumulation of one or more noxious materials selected from the group consisting of cadmium, arsenic, and herbicides as well as resistance to and accumulation of lead and comprising a nucleotide sequence encoding YCF1 polypeptide of SEQ ID NO:2; and ore preferably a YCF1 gene having the nucleotide sequence of SEQ ID NO:1. The YCF1 gene exists at the sixth chromosome In Saccharomyces cerevisiae. The YCF1 gene exhibits its function when expressed, and therefore the present invention is intended to encompass proteins having at least 28% homology, preferably at least 40% homology, and more preferably 50% homology with the amino acid sequence of the YCF1 protein and contributing to resistance to and accumulation of noxious materials, and DNA molecules encoding them.

YCF1 protein is one of the ABC transporter proteins, it exists at the vacuolar membrane in yeast, and it is known to mitigate the toxicity of cadmium by transporting cadmium conjugated with glutathione present within cytoplasm into the inside of vacuoles using MgATP as the energy source (Li, Z. S. et al. A new pathway for vacuolar cadmium sequestration in *Saccharomyces cerevisiae*: YCF1-catalyzed transport of bis(glutathionato)cadmium. *Proc. Natl. Acad. Sci. USA* 94, 42-47 (1997)).

Another example of a gene exhibiting resistance to and/or accumulation of noxious materials is the YHL035C gene, and a YHL035C gene exhibiting resistance to lead and comprising a nucleotide sequence encoding the polypeptide of SEQ ID NO:4, and more preferably the nucleotide sequence of SEQ ID NO:3, is provided. The YHL035C gene exists at the eighth chromosome in *Saccharomyces cerevisiae* and is one of the MRP-like ABC transporter proteins. The YHL035C gene exhibits its function when expressed, and therefore the present invention is intended to encompass proteins having at least 28% homology, preferably at least 40% homology, and more preferably 50% homology with the amino acid sequence of YHL035C protein and contributing to resistance to and accumulation of noxious materials, and DNA molecules encoding them.

In addition, the present invention provides a recombinant vector comprising said DNA molecule encoding the fungal MRP-like ABC transporter protein, and preferably it provides recombinant vectors comprising the YCF1 gene or YHL035C gene. Specific examples of the recombinant vectors include pESC-YCF1, ENpCambia-YCF1, or PBI121-YCF1 recombinant vectors, or the pESC-YHL035C recombinant vector, and pPBI121-YHL035C. The construction of these recombinant vectors can be conducted according to known processes by a person having ordinary knowledge in the art to which the invention pertains.

In the present invention, noxious materials can include heavy metals Including lead, cadmium, arsenic, etc., or agricultural chemicals and herbicides. The herbicides, which are generally lipophilic compounds having a low molecular weight, have been known to readily pass through plant cell walls and hinder plant-specific processes, for example, photosynthetic electron transport or biosynthetic metabolism of essential amino acids, etc., and for example, chlorosulfurone, axidofluorpen, norflurazon, and chloro-dinitrobenzene (CDNB) may be included.

Hence, transgenic organisms capable of exhibiting resistance to noxious materials as well as accumulating noxious materials can be prepared using the DNA molecules comprising nucleotide sequences encoding the polypeptide of YCF1 protein and YHL035C protein of the present invention, or DNA molecules having at least 28% homology therewith, and the transgenic organisms thus prepared can be employed to remediate sites polluted by noxious materials with ease and low cost.

In addition, the present invention relates to organisms transformed with said DNA molecules encoding the fungal MRP-like ABC transporter proteins. Also, the invention is directed to transgenic cells, preferably plant cells, which are transformed with said DNA molecules encoding the fungal MRP-like ABC transporter proteins. The ABC genes Include all of the foregoing genes, and as examples, the YCF1 gene and YHL035C gene are preferably employed.

The transgenic organisms are preferably prokaryotic or eukaryotic organisms, and as examples, plants, animals, yeast, *E. coli*, and fungus may be employed. Transgenic plants comprise heterogeneous DNA sequences according to genetic engineering methods, which are constructed to be properly expressed in plant cells, plant tissues, or plant bodies. Plant transformants can be prepared according to known techniques, and *Agrobacterium tumefaclens*-medlated DNA transfer is typically employed. More preferably, recombinant *agrobacterium* constructed by a method selected from the group consisting of electroporation, microparticle injection, and use of a gene gun is introduced into plants by a dipping method. In an embodiment of the present invention, transgenic plants can be prepared by constructing an expression cassette comprising the MRP-like ABC transporter protein coding sequence which is operably linked to permit its transcription and translation, constructing a recombinant vector comprising said expression cassette, and introducing said recombinant vector into plant cells or plant tissues.

The above plants include herbaceous plants such as *Arabidopsis*, rapes, leaf mustards, tobaccos, onions, carrots, cucumbers, sweet potatoes, potatoes, napa cabbages, radishes, lettuces, broccoli, petunias, sunflowers, grass, etc., and trees such as olive, willow, white birch, poplar, and birch, and preferably poplar and *Arabidopsis* are employed.

In a preferred embodiment of the present Invention, the transgenic organisms may include YCF1 *Arabidopsis thaliana* (accession number KCTC10064BP), YCF1 poplar, or YHL035C poplar. YCF1 *Arabidopsis thaliana* of the present invention was deposited with the Korean Collection for Type Cultures at the Korea Research Institute of Bioscience and Biotechnology located at 52, Eoun-dong, Yusung-gu, Daejeon, Korea on Sep. 5, 2001, and assigned Accession Number KCTC10064BP. YCF1 *Arabidopsis thaliana* can be asexually reproduced by tissue culture and grown into a plant according to conventional plant cell culturing methods and differentiation methods. YCF1 *Arabidopsis thaliana* is excellent in resistance to heavy metals and other noxious materials (FIGS. 6, 7, and 8) and accumulation thereof (FIG. 9), as compared with its wild-type counterpart, and in particular, it exhibits resistance to and accumulation of lead, cadmium, arsenic, and agricultural chemicals.

Figure 10:
FIGS. 10A-10C show a series of photographs (A,B) and a graph (C) showing that stem calli and leaf segments from YCF1-transformed poplar are enhanced in resistance to lead compared to those from wild type poplar.
Figure 10:
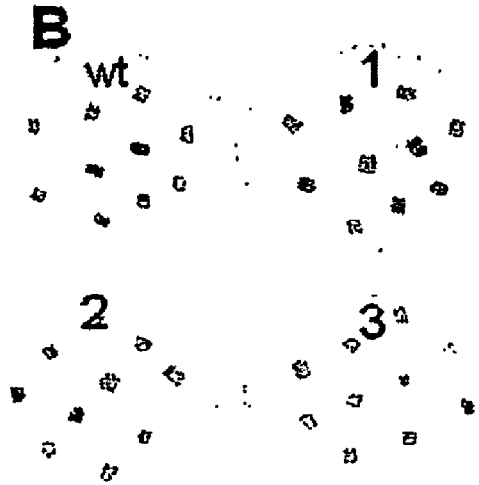
Figure 10:
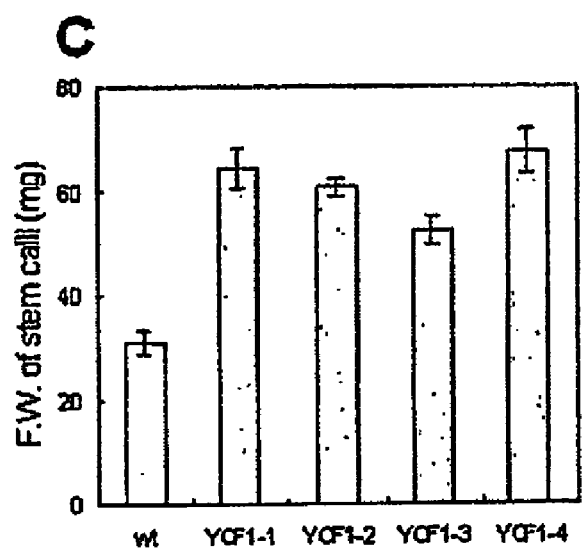
Figure 11:
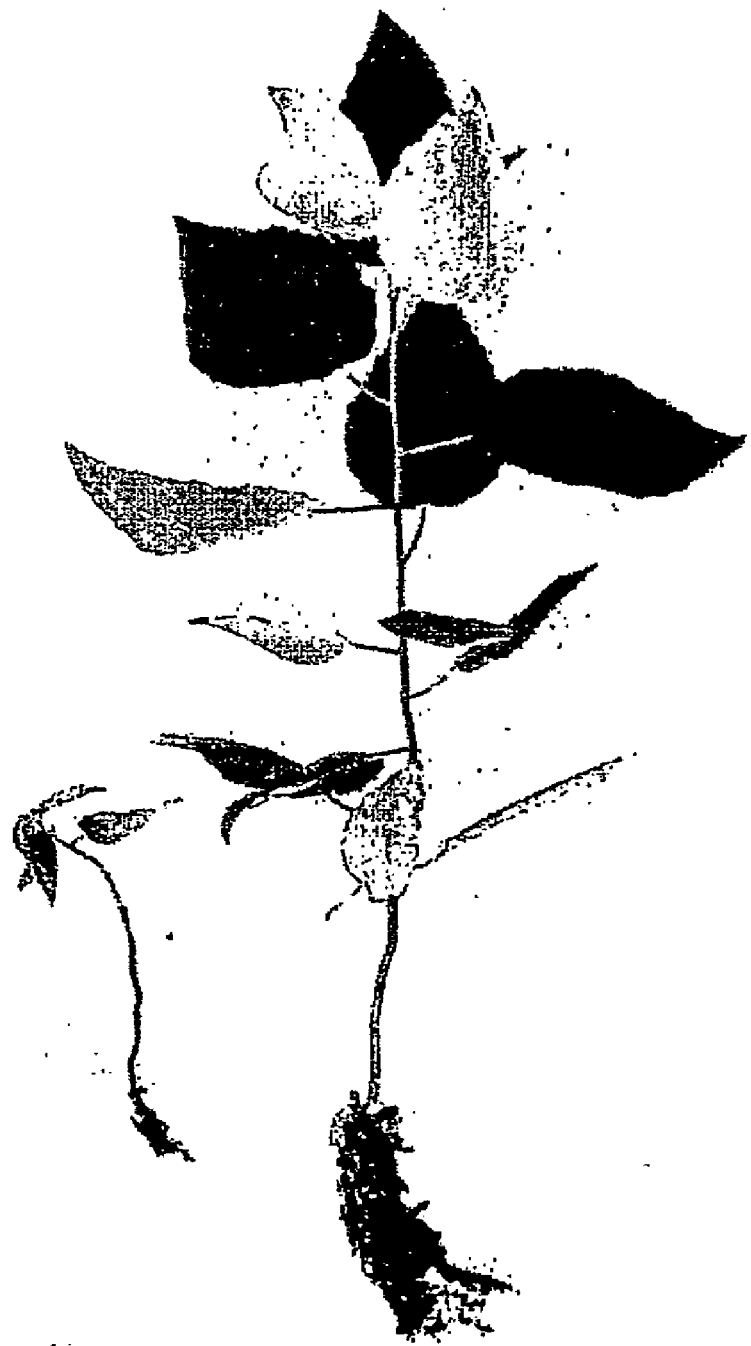
FIG. 11 shows a photograph showing that YHL035C-transformed poplar plant is more resistant to lead than wild type poplar plant.

YCF1 poplar and YHL035C poplar plants of the present invention can be asexually reproduced by tissue culture and grown into plants according to conventional plant cell culturing methods and differentiation methods. YCF1 poplar and YHL035C poplar plants are excellent in resistance to lead as compared with their wild-type counterparts (FIG. 10 and FIG. 11).

The preferred examples are hereinafter presented for better understanding of the invention. The following examples, however, are provided solely in order for better understanding of the present invention: the present invention should not be construed to be limited thereto.

EXAMPLE 1

Sensitivity to Lead and Cadmium in YCF1 Mutant Yeast

Wild-type yeast (DTY 165) and ycf1 mutant yeast (DTY 167, MATa ura3 leu2 his3 trp3 lys2 suc2 ycf::hisG) were cultured in YPD liquid media (1% yeast extract, 2% peptone, 2% dextrose) at 30° C. until OD600 reached 1-2, and then yeast cells of the same number ($1 \times 10^2$, $1 \times 10^3$, $1 \times 10^4$ or $1 \times 10^5$) were cultured in half-diluted YPD solid media containing 3 mM lead at 30° C. for three days. Likewise, they were also cultured in half-diluted YPD solid media containing 0.1 mM cadmium. The experimental results are shown in FIG. 1.

As shown in FIG. 1, the growth of ycf1 mutant yeast was decreased in 3 mM lead-containing media as compared with wild-type yeast, and ycf1 mutant yeast grew little in 0.1 mM cadmium-containing media. Therefore, it was verified that YCF1 is a gene conferring resistance against lead and admium.

EXAMPLE 2

Construction of Cloning Vector 2-1: Cloning Vector (PESC-YCF1)

For the isolation of the YCF1 gene, wild-type yeast was incubated in 3 ml YPD liquid media at 30° C. for 12 hours, and then centrifuged (12,000 rpm, 20-60 sec.). Resultant pellets were suspended in 400 μl of yeast lysis buffer (1 M sobitol, 0.1 M EDTA, 50 mM DTT (pH 7.5)), and after 40 μl of zymolase (5 mg/1 ml, 0.9 M sobitol) was added thereto, they were maintained at 37° C. for 15 to 30 minutes.

Subsequently, they were mixed with 400 ml of a urea buffer solution (7 M urea, 0.3125 M NaCl, 0.05 M Tris-HCl (pH 8.0), 0.02 M EDTA (pH 8.0), 1% Sarcosine) and then mixed with phenol/chloroform to isolate supernatants. The supernatants were mixed with 1 ml of 100% ethanol and centrifuged (12,000 rpm, 10 min.), and then the precipitated DNA was suspended in a TE buffer solution (10 mM Tris-HCl, 1 mM EDTA pH 8.0). PCR was performed using the isolated DNA as a template, YCFa primer (SEQ ID NO:3), YCFb primer (SEQ ID NO:4), and an LA taq polymerase kit (Takara) to isolate the YCF1 gene.

To prove that the YCF1 gene in yeast is associated with resistance to lead, the YCF1 gene isolated above (1) was cloned into a pESC-URA (yeast shuttle vector, Stratagene) vector. That is, YCF1 PCR products were cleaved with restriction enzymes Xho I and Sca I to prepare YCF1 (Xho I/Sca I), and a pESC-URA vector was digested with Hind III, treated with Klenow fragments and dNTPs to create a vector with blunt ends, and cleaved with restriction enzyme Xho I. The above YCF1 (Xho I/Sca I) and digested pESC-URA vector (Xho I/blunt-end) were ligated using T4 DNA ligase to construct the recombinant vector pESC-YCF1.

2-2: Cloning Vector (PESC-YHL035C)

The procedures were carried out in a manner substantially identical to Example 2-1 except that PCR was performed using yeast genomic DNA used in Example 2-1 as a template, YHL035Ca primer (SEQ ID NO:9), YHL035Cb primer (SEQ ID NO:10), and an LA taq polymerase kit (Takara) to isolate the YHL035C gene from yeast

```
YHL035Ca:
5'-cgacgcggccgcatgggaacggatcccttattatc-3'

YHL035Cb:
5'-cgacgcggccgocatcatcttacttgattgcttgg-3'
```

To express the YHL035C gene In yeast, a YHL035C gene was cloned into pESC-URA (yeast shuttle vector, stratagene). YHL035C PCR products were cleaved with Not I and ligated into pESC-URA using T4 DNA ligase to construct the recombinant vector pESC-YHL035C.

EXAMPLE 3

Resistance to Lead and Cadmium in YCF1 Recombinant Yeast

Recombinant yeast (ycf1-pESC yeast) where an empty vector was introduced into ycf1 mutant yeast, recombinant yeast (wt-pESC yeast) where an empty vector was introduced into wild-type yeast, and a recombinant yeast (ycf1-YCF1 yeast) where YCF1 was overexpressed in ycf1 mutant yeast were each constructed and tested for resistance to lead or cadmium.

3-1: Construction of YCF1 Recombinant Yeast

Yeast was inoculated into a 3 ml liquid YPC media and cultured at 30° C. for 12 hours, and then 0.5 ml of the culture was put Into 10 ml liquid YPD media and cultured at 30° C. for 6 to 8 hours until OD600 reached 0.5 to 0.8. The resultant culture were centrifuged (1,500 rpm, 5 min.) to collect yeasts, which was re-suspended in 5 ml of buffer (0.1 M LiOAc, TE, pH 7.5) and centrifuged. The centrifuged yeast was resuspended in buffer (0.1 M LiOAc, TE (pH 7.5)) and cultured in an agitating incubator at 30° C. for 1 hour, and after plasmid pESC, pESC-YCF1 or pESC-YCF1, and salmon testis DNA were added thereto, it was cultured at 30° C. for 30 minutes. The cultured yeast was mixed with 0.7 ml of buffer (40% PEG 3300, 0.1M LiOAc, TE (pH 7.5)) and incubated while shaking at 30° C. for 1 hour. Thereafter, the above mixture was placed at 42 to 45° C. for 5 minutes to be subjected to heat shock, and centrifuged (2,500 rpm, 5 min.) to collect yeast. The yeast was washed with 1 ml of TE buffer solution (pH 7.5), suspended In 0.2 ml of water or TE buffer solution (pH 7.5), and then cultured on selectable media (CM Ura7⁻) for 2 to 3 days to select transformed yeasts (ycf1-pESC yeast, wt-pESC yeast, ycf1-YCF1 yeast).

3-2: Resistance to Lead and Cadmium in Recombinant Yeast

The ycf1-pESC yeast, wt-pESC yeast, and ycf1-YCF1 yeast 25 constructed above were each cultured in galactose media (2% galactose, 1% of 0.17% YNB, 0.13% dropout powder, 0.5% ammonium sulfate) to which 1.8 mM lead was added, or in galactose media to which 50 uM of cadmium was added. Control group was cultured in galactose media without heavy metals. Growth degree of each of the recombinant ycf1-pESC yeast, wt-pESC yeast, and ycf1-YCF1 yeast in lead or cadmium-containing media is shown in the photographs of FIG. 2.

Figure 2:
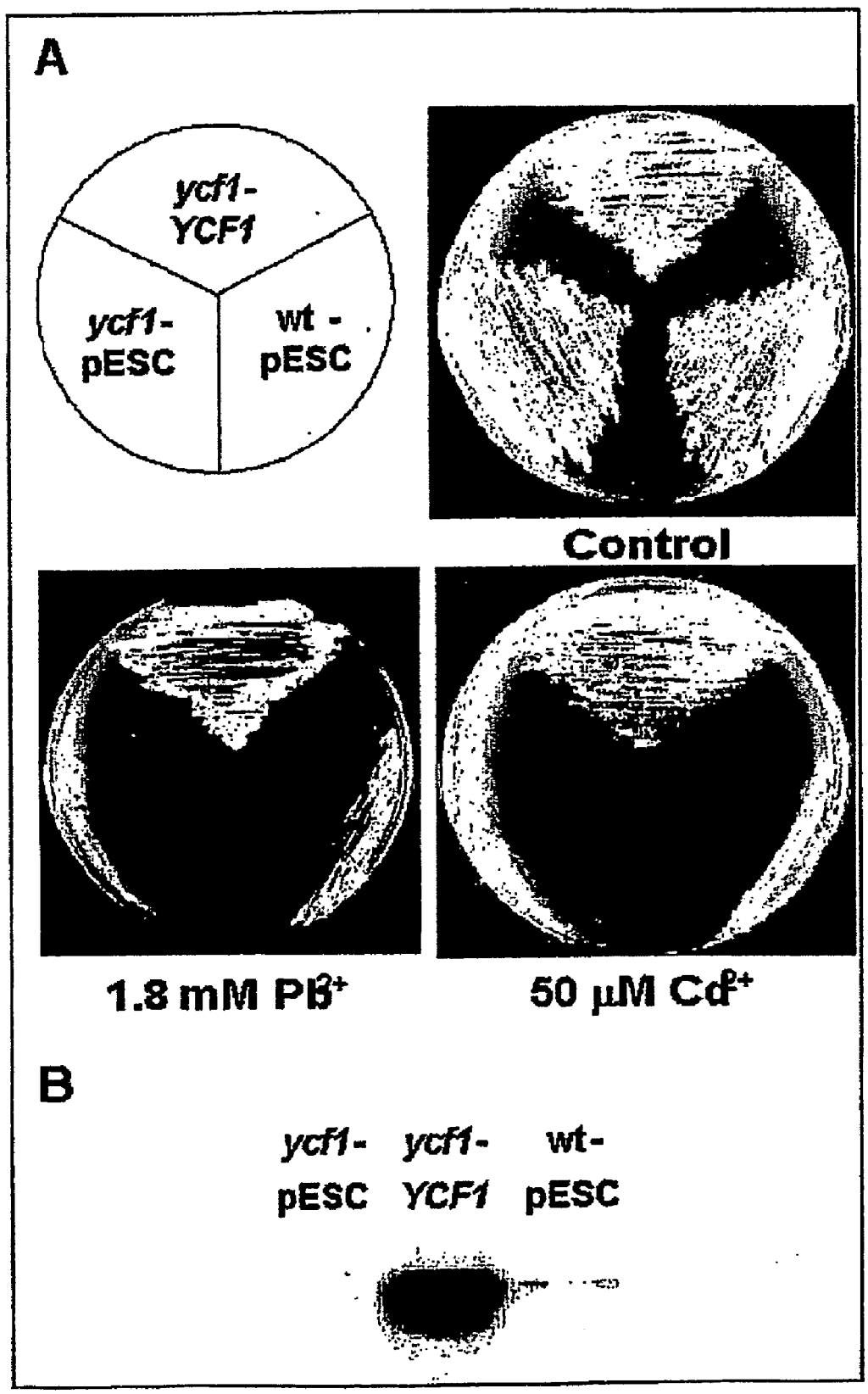
FIGS. 2A and 2B show photographs of wild type yeast transformed with empty vector (wt-pESC), ycf1 yeast transformed with empty vector (ycf1-pESC), and YCF1-transformed ycf1 (ycf1-YCF1) yeast growing on control, lead or cadmium-containing media (A), and the result from Northern blot of YCF1 mRNA from the yeast lines (B).

It can be seen from FIG. 2 that ycf1-YCF1 yeast where YCF1 was overexpressed in ycf1 mutant yeast grew better than ycf1-pESC yeast or wt-pESC yeast in media containing lead or cadmium, which thus supported the previous results that the YCF1 gene has an important role in conferring cadmium resistance. Additionally, it newly revealed that this gene is important to lead resistance.

3-3: YCF1 Expression in Recombinant Yeast

To investigate the expression of YCF1 in ycf1-pESC yeast, wt-pESC yeast, and ycf1-YCF1 yeast constructed in Example 3, Northern Blotting was performed.

Each recombinant yeast was ground with liquid nitrogen and total RNA extraction buffer solution (0.25 M Tris HCl pH 9.0, 0.25 M NaCl, 0.05 M EDTA, 0.345 M p-Aminosalicylic acid, 0.027 M triisopropyl naphthalene sulfonic acid, 0.02% β-mercaptoethanol, 0.024% phenol) was mixed with phenol/chloroform in a 1:1 ratio. The supernatants obtained from centrifugation at 12,000 rpm for 10 minutes were transferred into a new tube, to which 400 μl of isopropanol was added. Centrifugation was performed again at 12,000 rpm for 10 minutes to precipitate RNA, which was then lysed in DEPC-treated water and stored in a freezer.

To perform Northern Blot, 30 μg of RNA was electrophoresed on agarose gel for RNA and transferred onto a nylon membrane. The nylon membrane was incubated while stirring in a hybridization reaction solution (6×SSPE, 0.5% SDS, 10% PEG, 1% nonfat milk, 50% formamide) at 42° C. for 2 hours. Then, YCF1 labeled with $^{32}$P dCTP was added thereto and the reaction was performed at 42° C. for 12 hours. After the hybridization reaction, the nylon membrane was washed twice with a buffer (2×SSPE and 0.5% SDS), washed with another buffer (0.2×SSPE, 0.5% SDS), dried, and then autoradiographed on X-ray film. The experimental results are shown in FIG. 2B.

From FIG. 2B, Northern Blot photographs of three kinds of recombinant yeasts, it can be seen that ycf1-YCF1 yeast overexpressed YCF1 mRNA. That is, it was proven that lead and cadmium resistance in ycf1-YCF1 yeast, which was exhibited in Example 3-2, is due to the overexpression of YCF1.

3-4: Lead and Cadmium Resistance Mechanism

To investigate whether lead and cadmium resistance conferred by the YCF1 gene is due to the intracellular accumulation of heavy metals or due to extracellular discharge, experiments were conducted.

Figure 3:
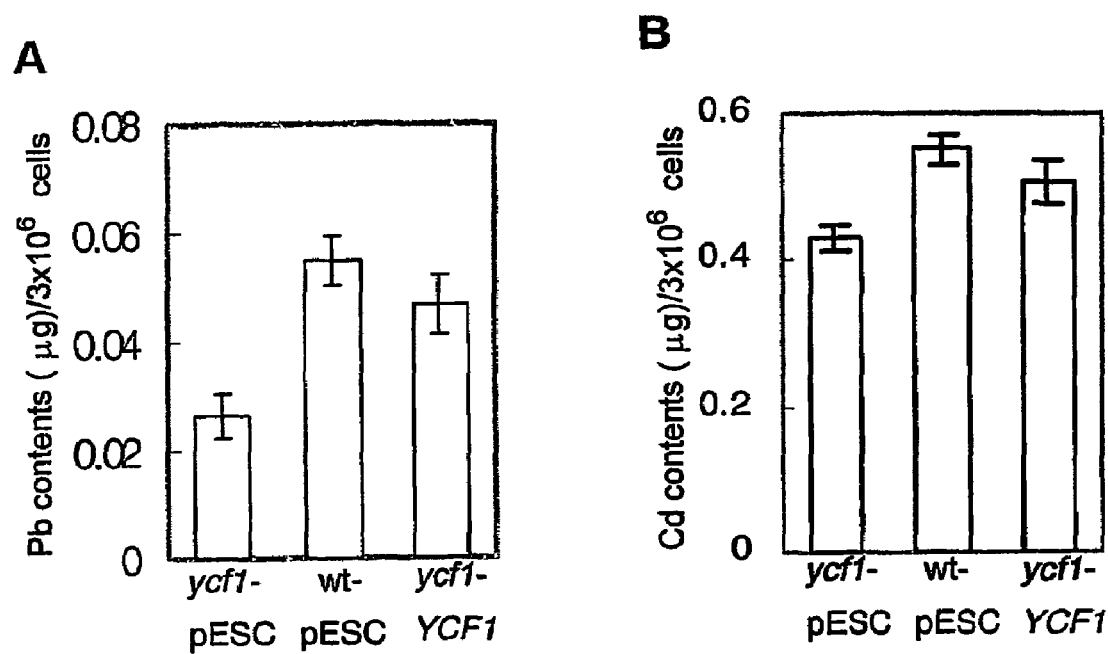
FIGS. 3A and 3B show graphs of lead (A) or cadmium (B) content in ycf1-pESC yeast, wt-pESC yeast, and ycf1-YCF1 yeast.

Three kinds of yeasts (ycf1-pESC yeast, wt-pESC yeast, and ycf1-YCF1 yeast) were each cultured in 1/2 galactose solid media containing 1.5 mM lead or 15 uM cadmium for one day, and the cultured yeasts were scraped for harvest. The harvested yeasts were put into 1 ml of concentrated nitric acid, digested for 200° C. for about 6 hours, and then diluted with 10 ml of 0.5 N nitric acid, and the amount of heavy metals contained in the yeasts was measured using an atomic absorption spectrometer (AAS). The measurement results for ycf1-pESC yeast, wt-pESC yeast, and ycf1-YCF1 yeast are represented by graph In FIG. 3.

Consequently, wt-pESC yeast and ycf1-YCF1 yeast showed a high accumulation of lead and cadmium as compared with ycf1-pESC yeast, and in particular, wt-pESC yeast and ycf1-YCF1 yeast exhibited about a 2-fold higher accumulation of lead than ycf1-pESC yeast. Therefore, it was verified that lead and cadmium resistance of the YCF1 gene is due to Intracellular accumulation of these heavy metals.

EXAMPLE 4

Lead Resistance in YHL035C Recombinant Yeast 4-1: Construction of Recombinant Yeast Recombinant yeast (yhl035c-v yeast) where an empty vector was introduced into yhl035c mutant yeast, recombinant yeast (wt-v yeast) where an empty vector was introduced Into wild-type yeast, and recombinant yeast (YHL035C yeast) where YHL035C was overexpressed in yh1035c mutant yeast were each constructed according to methods substantially similar to the above Example 3-1, and transformed yeasts (wt-v yeast, yh1035c-v yeast, YHL035C yeast) were selected. Resistance to lead was tested using these recombinant yeasts.

4-2: Lead Resistance Test in Recombinant Yeast

Resistance to lead in wt-v yeast, yhl035c-v yeast, and YHL035C yeast was tested according to methods substantially similar to the above Example 3-2. The growth degree of each of the recombinant wt-v yeast, yh1035c-v yeast, and YHL035C yeast in lead-containing media is exhibited by photographs in FIG. 4.

Figure 4:
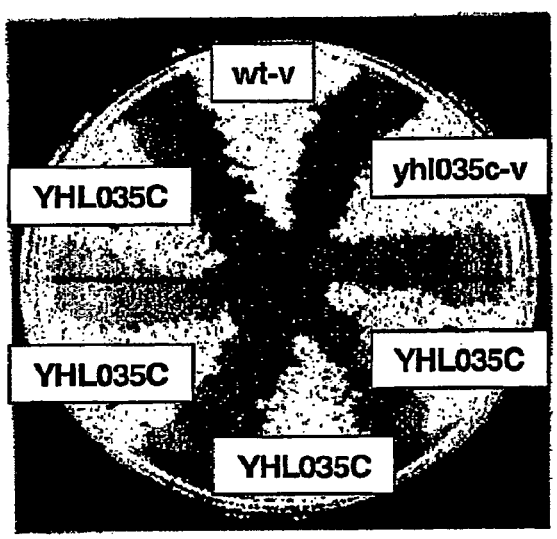
FIG. 4 shows photographs of wild type, YHL035C mutant (yhl035C-v), and YHL035C-transformed yhl035C-v yeasts growing on control or lead-containing media, and shows that yhl035C-v yeast is more sensitive to lead than wild type or yhl035C-v yeast transformed with YHL035C.
Figure 4:
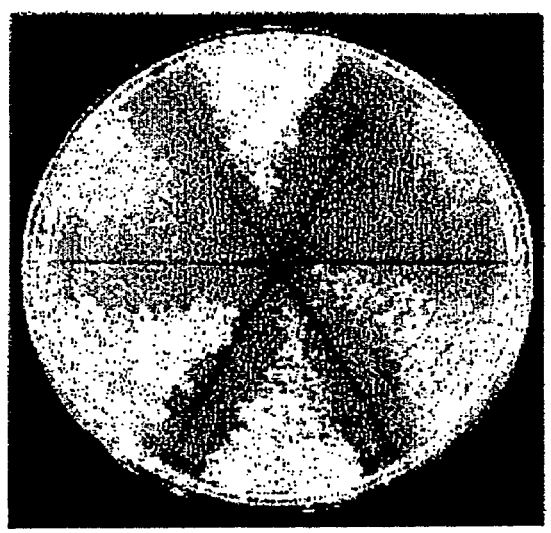

As can be seen in FIG. 4, yhl035c-v, which is a yhl035c mutant yeast, was more sensitive than wt-v yeast in media containing 1.8 mM lead. However, YHL035C yeast, where YHL035C was expressed in yhl035c mutant yeast, again recovered resistance to lead and exhibited growth similar to that of wt-v yeast In media containing 1.8 mM lead. Hence, it newly revealed that the YHL035C gene has an important role in conferring lead resistance.

EXAMPLE 5

Preparation of Transgenic Plants 5-1: Construction of YCF1 Vector and YHL035C Vector for Plant Transformation To introduce YCF1 gene into plants, 4.6 kb of YCF1, which is a BamHI/SnaB I fragment of pESC-YCF1 plasmid, was inserted into PBI121 (BamH I/Sma I) whereby a PBI121-YCF1 vector was constructed. To improve the expression of the YCF1 gene, an EnPCAMBIA1302-YCF1 vector was constructed. A PCAMBIA1302 vector was digested with restriction enzyme SalI and treated with Klenow fragments and dNTPs to create a vector with blunt ends, and 35S enhancer (BamHI/blunt-end) was inserted into the vector, which was digested with BamHI, to construct the EnPCAMBIA1302 vector. The EnPCAMBIA1302-YCF1 vector was constructed by the insertion of a YCF1 gene (BamHI/blunt-end) at site BglII/PmlI of the EnPCAMBIA1302 vector.

PBI121-YCF1 and EnPCAMBIA1302-YCF1 vectors were introduced into *E. coli* using an electroporator (BIO-RAD) and cultured on LB solid media. A single colony was inoculated in 3 ml LB (Amp) liquid media, cultured for 12 to 16 hours, and centrifuged to harvest the transformed *E. coli*. Then, 100 ul of solution I (50 mM glucose, 25 mM Tris-HCl (pH 8.0), 10 mM EDTA) was added to the harvested *E. coli* to re-suspend it, 200 ul of solution II (1% SDS, 0.2 N NaOH) was added thereto, the mixture was gently mixed, and then incubated on ice water for 5 minutes. Then, 150 ul of Solution III (5 M Potassium acetate) was added to the above mixture, which was then slowly mixed 3 to 5 times and centrifuged (12,000 rpm, 10 min.) to collect the supernatant. The supernatant was mixed with 100% ethanol to precipitate DNA, which was then isolated and dried. The PBI121-YCF1 plasmid DNA thus obtained was lysed in TE buffer solution and cut with restriction enzymes BamHI and EcoRI, and the insertion of the YCF1 gene in the correct orientation was confirmed.

To introduce the YHL035C gene into plants, a pHI121-YHL035C vector was constructed according to methods substantially similar to those used in the construction of the above YCF1 vector for plant transformation, except that the YHL035C gene was cut out from the pESC-YHL035C vector constructed in Example 2 and restriction sites SacI and EcoICR1 were created at both termini thereof, which were then put Into a pBI121 vector digested with SacI and SmaI to construct the pBI121-YHL035C vector.

5-2: Preparation of Transgenic *Arabidopsis thaliana*

The vectors PBI121-YCF1 and EnPCAMBIA1302-YCF1 constructed in the above Example 5-1 were introduced into Agrobacterium (LBA4404). The transformed *Agrobacterium* was screened on MS (Murashige-Skoog) media containing kanamycin, and transfected Into the flower of *Arabidopsis thaliana* by a dipping method (Clough, S. J., and Bent, A. F., Floral dip: a simplified method for *Agrobacterium*-mediated transformation of *Arabidopsis thaliana. Plant J.* 16, 735-743 (1988)) to Introduce the YCF1 gene into the plants. After 4 to 5 weeks, the seeds of the *Arabidopsis* plants were harvested and selected for YCF1 *Arabidopsis* plants using kanamycin for plants transformed with the PBI121-YCF1 vector and hygromycin for plants transformed with the EnPCAMBIA1302-YCF1 vector.

Figure 5:
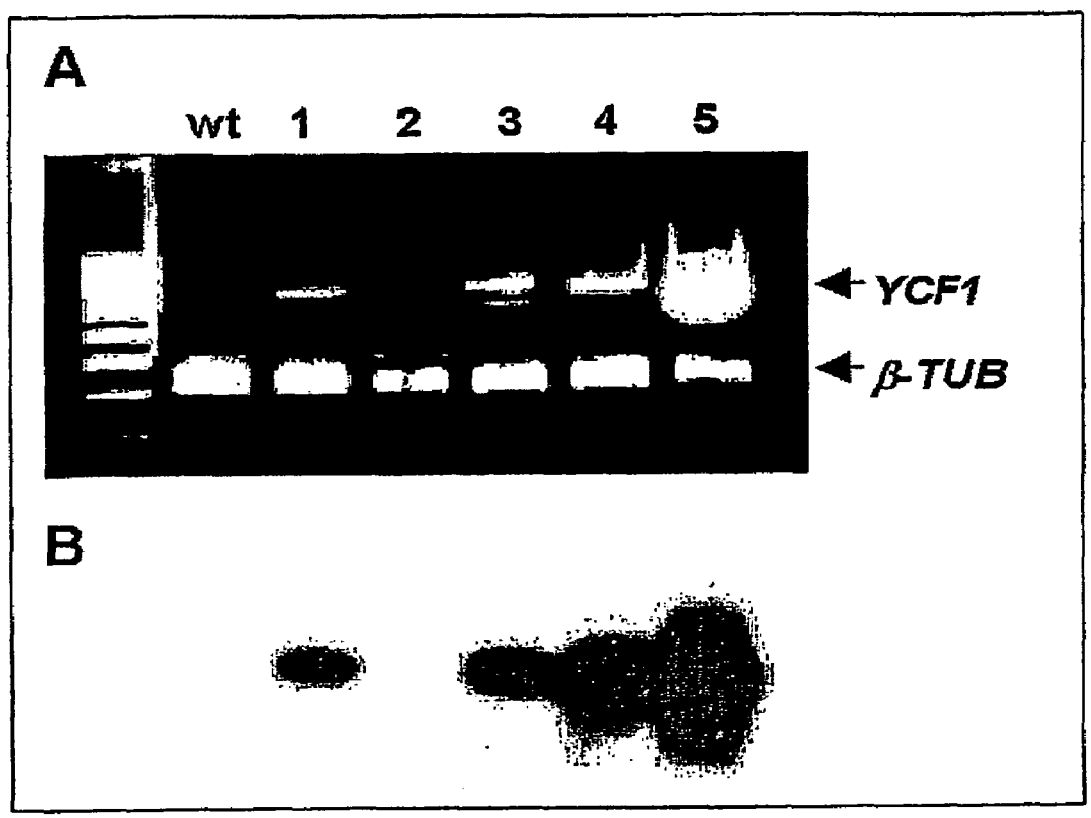
FIGS. 5A and 5B show photographs of RT-PCR results, which show the expression of YCF1 in YCF1-transformed *Arabidopsis thaliana*.

A total of five lines of YCF1 *Arabidopsis* plants were obtained, and they were tested for expression levels of YCF1 mRNA, and whether the expressed mRNA included the C-terminal 700 bp of YCF1 mRNA to ensure that the full length mRNA was expressed. First, mRNA was extracted from the five lines of YCF1 *Arabidopsis* plants and subjected to RT-PCR using the primers of SEQ ID NO:5/SEQ ID NO:6, and the RT-PCR results are exhibited in FIG. 5A. As shown in FIG. 5A, 700 bp of YCF1 are expressed in plants 1, 3, 4, and 5, and in plants 4 and 5, YCF1 was highly expressed.

Southern Blotting was carried out for the above RT-PCR products, and the results are exhibited in FIG. 5B. It can be seen from FIG. 5B that the gene expressed in plants 1, 3, 4, and 5 in FIG. 5A is YCF1, and the complete transcription of wild-type YCF1 mRNA occurred, confirming the conclusion from FIG. 5A. This YCF1 *Arabidopsis thaliana* showing high YCF1 expression was deposited to the Korean Collection for Type Cultures at the Korea Research Institute of Bioscience and Biotechnology located at 52, Eoun-dong, Yusung-gu, Daejeon, Korea on Sep. 5, 2001, and assigned Accession Number KCTC10064BP.

5-3: Preparation of Transgenic Poplar

As plants for transformation, Bong-hwa 1, a clone of hybrid poplar (*Populus alba* ×*P. glandulosa*), which does not bloom outdoors, was used after proliferation. To ensure in vitro aseptic materials of poplar, a stalk was obtained from clone bank which was being conserved in nursery at the Korea Forest Research Institute, and surface-sterilized with ethanol (5 minutes) and 2% NaCl (20 min.), and then the stalk, which was developed after 4-weeks of cultivation on MS media, was employed as a specimen for transformation.

For transformation using *Agrobacterium* containing a gene of Interest, Induction of a callus, and induction of the stalk, etc., the method by Noh et al. (Genetic Engineering of Poplar (2002), written by Noh, Eun-un et al. ISBN#89-8176-098-5 93520) was used. *Agrobacterium tumefaciens* constructed In Example 5-2, into which PBI121-YCF1 and EnPCAMBIA1302-YCF1 vectors were introduced, was inoculated in LB media and cultured overnight at 30° C., and after centrifugation at 1,000 g for 10 minutes, the media were discarded and the pellet was re-suspended in a 0.85% NaCl solution. The suspension was poured into a petri dish, and then the internode tissue of poplar cultivated in vitro was dipped thereinto for 20 minutes. After that, it was placed between two disinfected absorption filtering papers and gently pressed to eliminate excessive *Agrobacteria*, and then they were co-cultivated in callus-inducible media containing no antibiotic (MS+2.4-D 1.0 mg/L, BA 0.1mg/L, NAA 0.01 mg/L) (Murashige and Skoog. 1962) for 2 days followed by the selection of transformed cells by use of selectable media containing 50 mg/L kanamycin and 500 mg/L cefotaxime.

The callus thus formed was grown in stalk-inducible media (WPM+zeatin 1.0 mg/L, BA 0.1 mg/L, NAA 0.01 mg/L) (Lloyd and McCown, 1981) containing 50 mg/L of kanamycin to induce stalks. Once the stalks were induced, they were induced to elongate through subcultures in MS basic media containing 50 mg/L kanamycin, and roots were induced by addition of 0.2 mg/L of IBA to the same media, thus obtaining the whole plant body.

EXAMPLE 6

Growth of Transformed *Arabidopsis* Plants in the Presence of Noxious Materials

YCF1 *Arabidopsis* plants prepared in Example 5 were cultivated in 1/2 MS media containing lead (0.9, 1, 1.1 mM), cadmium (50, 60, 70 μM), herbicide chloro-dinitrobenzene (CDNB) (60 μM), and pentavalent arsenic (50 μM) to investigate their growth degree. As a control, *Arabidopsis* plants transformed with an empty vector (PBI) and wild-type plants were used. The experimental results are shown in FIG. 6 to FIG. 8.

Figure 6:
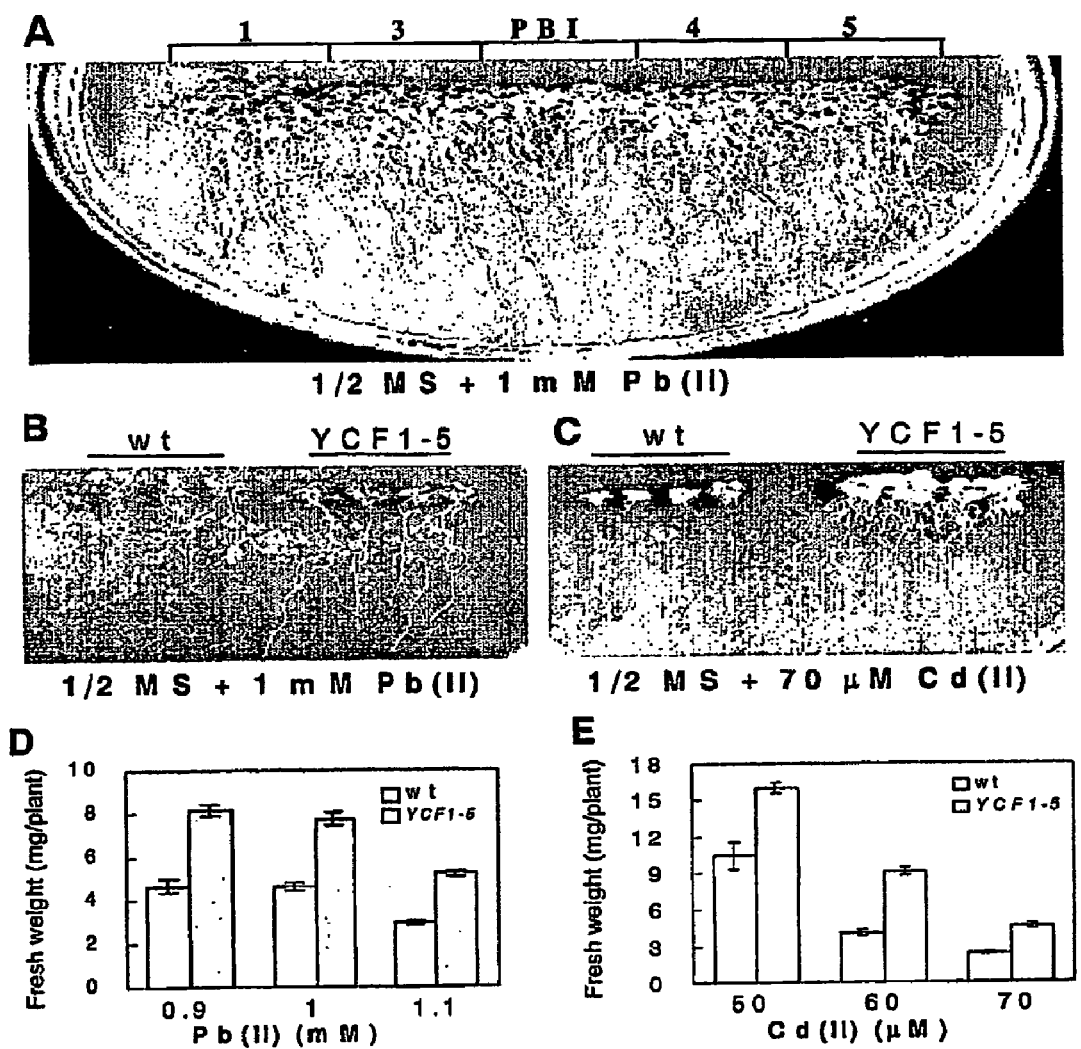
FIG. 6 shows photographs (A,B,C) and graphs (D,E) showing that YCF1-transformed *Arabidopsis thaliana* are enhanced In resistance to lead and cadmium.

FIG. 6 shows photographs and graphs exhibiting growth of YCF1-transformed *Arabidopsis thaliana*. As shown in FIG. 6, when YCF1 *Arabidopsis* and control plants were grown in media containing lead for three weeks, YCF1 *Arabidopsis* (1, 3, 4, and 5) showed less chlorosis In leaves and better growth of roots than PBI empty vector transformed plants and wild-type plants (A, B, and D). Also, when YCF1 and wild-type *Arabidopsis* plants were grown in cadmium media at various concentrations, wild-type *Arabidopsis* plants showed more chlorosis in leaves and their roots grew poorly and were shorter than the YCF1 transformants (C and E).

Figure 7:
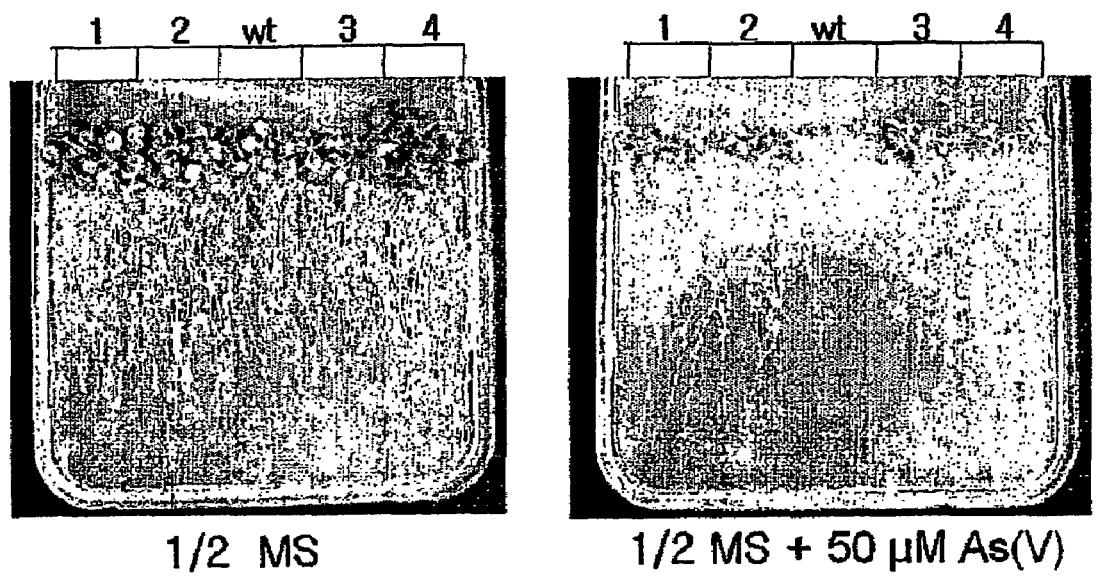
FIG. 7 shows photographs showing that YCF1-transformed *Arabidopsis thaliana* are enhanced in resistance to arsenic.

FIG. 7 shows photographs exhibiting resistance to arsenic In YCF1-transformed *Arabidopsis thaliana*. When grown in media containing 60 μM pentavalent arsenic for three weeks, wild-type *Arabidopsis* showed a little growth, whereas YCF1 transformants (1, 2, 3, and 4) showed much better growth as compared with wild-type.

Figure 8:
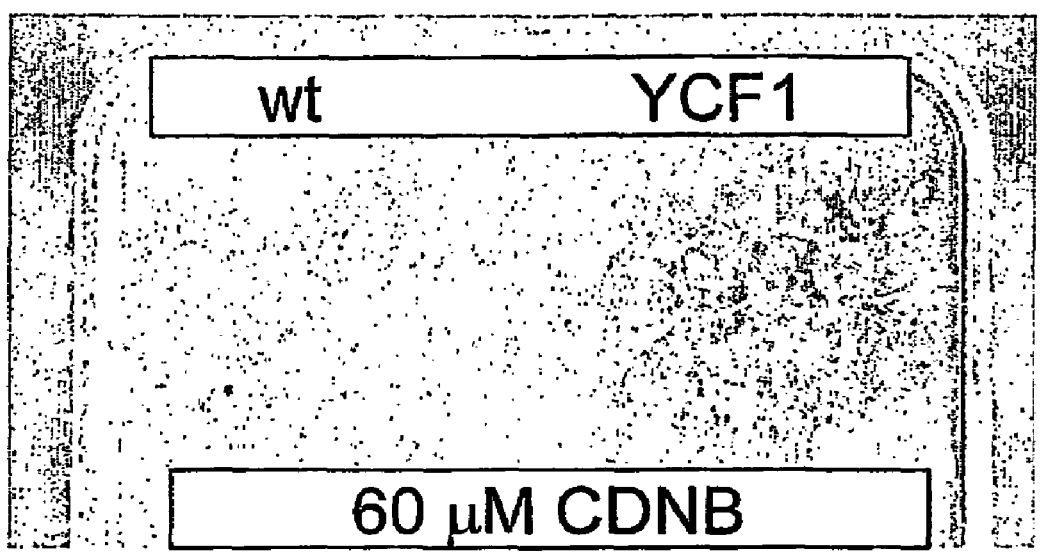
FIG. 8 shows a photograph showing that YCF1-transformed *Arabidopsis thaliana* are enhanced in resistance to herbicide CDNB.

FIG. 8 shows a photograph exhibiting resistance to CDNB in YCF1-transformed *Arabidopsis thaliana*. When YCF1 *Arabidopsis* and control plants were grown in media containing 60 μM CDNB for two months, wild-type plants showed poor germination and almost died, whereas YCF1 *Arabidopsis* plants grew well, almost like *Arabidopsis* plants grown in normal condition.

Hence, it was verified that YCF1-transformed *Arabidopsis thaliana* prepared in Example 5 has resistance to lead, cadmium, arsenic, and herbicides.

EXAMPLE 7

Accumulation of Heavy Metals in Transformed *Arabidopsis* Plants

Figure 9:
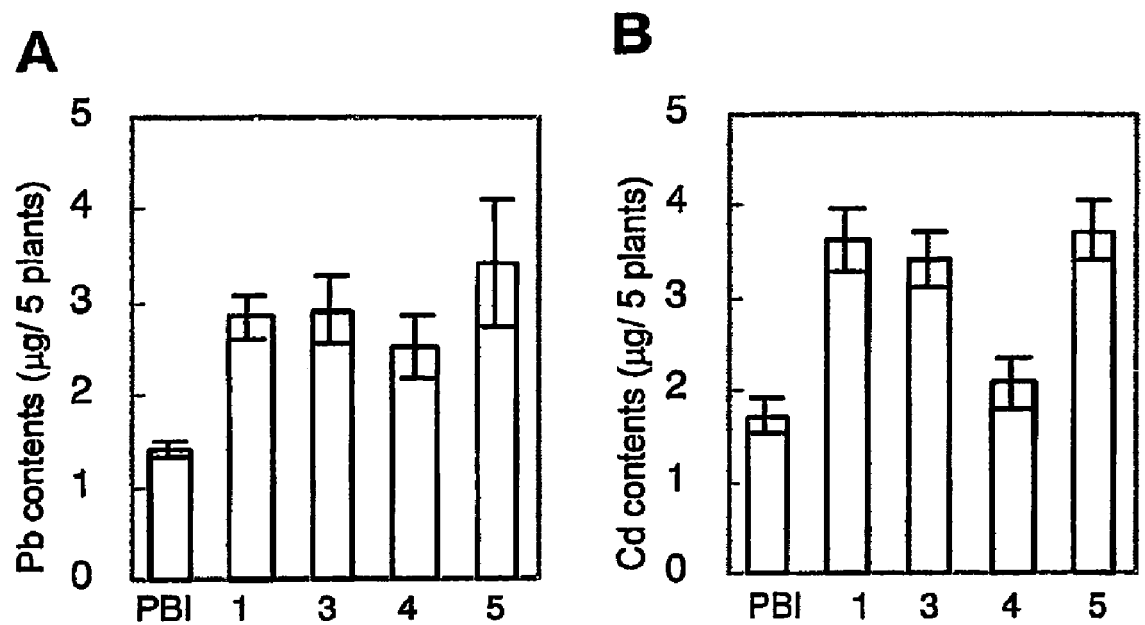
FIGS. 9A and 9B show graphs of lead (A) and cadmium (B) content in YCF1-transformed *Arabidopsis thaliana*.

YCF1 *Arabidopsis* plants obtained in Example 5 and wild-type *Arabidopsis* transformed with empty vector, PBI, were cultivated in 1/2 MS media containing lead (0.75 mM) and cadmium (70 μM) for three weeks to investigate accumulation of heavy metals. The amount of accumulation of lead or cadmium was investigated by experiments substantially similar to Example 6, and the results are shown in FIG. 9, in which FIG. 9A shows the lead content and FIG. 9B shows the cadmium content of the plants.

As shown in FIG. 9A, YCF1 *Arabidopsis* plants showed 2-fold or 1.4-fold higher accumulation of lead than PBI. Also, as shown in FIG. 9B, YCF1 *Arabidopsis* plants showed 2-fold or 3-fold higher accumulation of cadmium than PBI.

Hence, it was verified that YCF1 *Arabidopsis* plants have higher accumulation of lead and cadmium than wild-type *Arabidopsis*.

EXAMPLE 8

Mechanism of Resistance to Noxious Materials in YCF1-Transformed Plants

YCF1-transformed plants showed resistance to lead, cadmium, arsenic, and herbicides and showed accumulation of lead and cadmium. To Investigate that these phenomena occurred due to the fact that YCF1 proteins transport heavy metals into vacuoles, the vacuoles were separated from YCF1 transformed plants and wild-type plants, and experiments of transporting cadmium and herbicides were carried out. The transport experiment results of cadmium (Cd+ GSH) and herbicides (DNB-GS) in the vacuoles of the YCF transformed plants and wild-type plants are shown in Table 1 below.

TABLE 1

Accumulation of GS-associated Compounds in the Vacuoles Separated from Arabidopsis (unit: pmol/1 ul vacuole/20 min)

| | Wild-type Plants | | YCF1 Transformed Plants | |
|---|---|---|---|---|
| Compounds | −MgATP | +MgATP | −MgATP | +MgATP |
| DNB − GS | 21 ± 1.1 | 28 ± 1.3 | 24 ± 0.9 | 33 ± 1.2 |
| Cd + GSH | 75 ± 3.3 | 104 ± 4.9 | 71 ± 3.4 | 177 ± 9.8 |
| GSH | — | 70 ± 2.2 | — | 69 ± 1.1 |

As shown in Table 1 above, as YCF1 employs MgATP as its energy source when transporting materials, there was, in the −MgATP group, no difference in cadmium (Cd+GSH) and herbicide (DNB-GS) contents between YCF1 transformants and wild-type plants. However, when MgATP was added, YCF1 transformants' vacuoles showed about a 1.7-fold higher accumulation of cadmium (Cd–GSH) than the wild-type vacuoles. In case of the herbicide (DNB-GS), YCF1 transformants showed a little higher accumulation than wild-type.

It was verified from FIGS. 6, 7, 8, and 9 that YCF1 transformed *Arabidopsis* plants have higher resistance to lead, cadmium, arsenic, and herbicides than wild-type, and they accumulate more lead and cadmium. It was supported from the results of Table 1 that such phenomenon is due to the fact that YCF1 proteins expressed in the vacuoles of YCF1 transformed *Arabidopsis* plants transport cadmium and herbicides into the vacuoles and stabilize them, thereby conferring resistance to and accumulation of those noxious materials.

EXAMPLE 9

Growth of Transgenic Poplar Plants 9-1: YCF1 Transgenic Poplar Plants

The leaf fragments and stalks of YCF1 poplar plants prepared in Example 5 were mounted on callus-inducible media containing 500 ppm of lead, and cultivated for two weeks to Investigate the difference In their growth. As a control, wild-type poplar plants, which were not transformed, were treated in the same manner, and the results of the experiments are shown in FIG. 10. FIG. 10 shows photographs and a graph showing the growth of YCF1 transformed and control poplar plants.

As shown in FIG. 10, in media containing lead, YCF1 poplar (1, 2, 3, and 4) showed about a 2-fold higher growth in stalk pieces than wild-type (wt) (A and C), and the leaf fragments of YCF1 poplar (1, 2, and 3) showed less browning than those of wild-type (wt) and kept the color of chlorophyll green (B).

9-2: YHL035C Transformed Poplar Plants

YHL035C transformed poplar plants prepared in Example 5 were transferred to a pot and allowed to grow into pot seedlings. These pot seedlings were transferred to soil that was dipped into a solution containing 500 ppm of $Pb(NO_3)_3$. The results of the experiment are shown in FIG. 11.

FIG. 11 shows a photograph showing that wild-type poplar grew poorly when cultivated in soil containing lead for four weeks, whereas the YHL035C transformant poplar grew much better than the wild-type. Hence, It was verified that YCF1 transformed poplar plants and YHL035C poplar plants prepared in Example 5 have resistance to lead.

As described above, the YCF1 gene of the present invention Improves resistance to and accumulation of heavy metals and other noxious materials, and the YHL035C gene improves resistance to lead, and accordingly, the transformants capable of expressing these genes can be used for the purpose of remediating environments polluted with noxious materials. Thus, the transformants of the invention provide an environmentally-friendly way to remediate the environment at a low cost.

What is claimed is:

1. A transgenic organism transformed with a DNA molecule encoding the protein YHL035C having the sequence of SEQ ID NO:4, wherein the DNA molecule comprises a pESC-YHL035C recombinant vector or a pPBI121YHL035C recombinant vector, wherein said organism is plant or yeast, and wherein said organism exhibits resistance to and enhanced accumulation of lead.

2. The transgenic organism according to claim 1, wherein said plant is selected from the group consisting of *Arabidopsis*, rape, leaf mustard, tobacco, onion, carrot, cucumber, sweet potato, potato, napa cabbage, radish, lettuce, broccoli, petunia, sunflower, grass, white birch, poplar, olive, willow, and birch.

3. The transgenic organism according to claim 2, wherein said plant is poplar.

4. A plant cell exhibiting resistance to and enhanced accumulation of lead transformed with the DNA molecule encoding the protein YHL035C having the sequence of SEQ ID NO:4, wherein the DNA molecule comprises a pESC-YHL035C recombinant vector or a pPBI 121-YHL035C recombinant vector.

5. The plant cell according to claim 4, wherein said plant cell is from a plant selected from the group consisting of *Arabidopsis*, rape, leaf mustard, tobacco, onion, carrot, cucumber, sweet potato, potato, napa cabbage, radish, lettuce, broccoli, petunia, sunflower, grass, white birch, poplar, olive, willow, and birch.

6. A method of preparing a transgenic organism exhibiting resistance to and enhanced accumulation of lead, the method comprising transforming an organism with a DNA molecule encoding the protein YHL035C having the sequence of SEQ ID NO:4 or with a recombinant vector selected from the group consisting of pESC-YHL035C and pPB1121-YHL035C, and wherein said organism is a plant, or yeast.

* * * * *

SEQUENCE LISTING

```
<160> NUMBER OF SEQ ID NOS: 10

<210> SEQ ID NO 1
<211> LENGTH: 4548
<212> TYPE: DNA
<213> ORGANISM: Saccharomyces cerevisiae
<220> FEATURE:
<221> NAME/KEY: gene
<222> LOCATION: (0)...(0)
<223> OTHER INFORMATION: ycf1 gene

<400> SEQUENCE: 1
atggctggta atcttgtttc atgggcctgc aagctctgta gatctcctga agggtttgga        60
cctatatcct tttacggtga ctttactcaa tgcttcatcg acggtgtgat cctaaatcta       120
tcagcaattt tcatgataac cttcggtatc agagatttag ttaacctttg caagaaaaaa       180
cactctggca tcaaatatag gcggaattgg attattgtct ctaggatggc actagttctg       240
ttggagatag cgtttgtttc acttgcgtct ttaaatattt ctaaagaaga agcggaaaac       300
tttaccattg taagtcaata tgcttctaca atgttatctt tatttgttgc tttagcctta       360
cactggatag aatacgatag atcagttgta gccaatacgg tacttttatt ctattggctt       420
tttgaaacat tcggtaattt tgctaaacta ataaatattc taattagaca cacctacgaa       480
ggcatttggt attccggaca aacgggtttc atactaacgt tattccaagt aataacatgt       540
gccagtatcc tgttacttga agctcttcca aagaagccgc taatgccaca tcaacacata       600
catcaaactt taacaagaag aaaaccaaat ccatacgata gcgcaaacat attttccagg       660
attaccttct cttggatgtc aggtttgatg aaaactggct atgaaaaata cttagtgaaa       720
gcagatttat ataaattacc gaggaacttt agtagtgaag aactctctca aaaattggag       780
```

-continued

```
aaaaactggg aaaatgagtt gaagcaaaaa tcaaatcctt cattatcatg ggctatatgc    840 agaactttg gatctaaaat gcttttagcc gcattcttta aagcaattca tgatgttcta    900
gcatttactc aaccacaact actaaggatt ttaatcaagt tcgtcacaga ctataacagt    960
gagagacagg atgaccattc ttctcttcaa gggtttgaaa ataaccaccc acaaaaatta   1020
cccattgtaa gagggttttt gattgcgttt gctatgtttc tggtgggctt tactcagaca   1080
tctgtcctgc atcaatattt cctgaatgtc ttcaacacag gcatgtatat aagagcgcc   1140 ctaacggctt taatatatca aaaatcctta gtgctatcta atgaggcttc tggactttcc   1200
tctaccggtg acattgtcaa tctcatgagt gtggatgttc aaaaattaca agatttaaca   1260
caatggctaa atttaatatg gtcagggcct tttcaaatca ttatttgctt atattctctg   1320
tataagttgt tgggaaattc catgtgggtt ggcgtgatta tactagttat tatgatgcca   1380
ttgaactcat ttttgatgag gatacaaaag aagttgcaaa atcccagat gaagtacaaa    1440 gatgaaagga cccgtgttat aagtgaaata ctaaacaata ttaaatcttt gaagttatat   1500
gcatgggaga agccttatag ggaaaagcta aagaagtaa gaataacaa agagttaaaa    1560 aatcttacaa aactaggatg ttatatggct gtgacaagtt ttcagttcaa tatagtacca   1620
ttccttgttt catgttgtac ctttgctgta tttgtttata ctgaggatag agcattgact   1680
actgacttag ttttccctgc tttgactctg ttcaacctgc tctcattccc actaatgatt   1740
attcctatgg ttttaaattc ttttatcgaa gcttctgttt ctattggtag attatttaca   1800
ttctttacca atgaagagct acaaccagat tcggttcagc gttaccaaa agtaaaaaat    1860 attggcgatg tagccattaa cattggagat gatgctacct ttttatggca acggaaaccg   1920
gaatacaaag tagcccttaaa gaatattaat ttccaagcta aaaaaggaaa tttgacctgt   1980
attgttggta agttggcag tggtaaaaca gctctattgt catgcatgtt aggtgatcta   2040
ttcagggtta aaggtttcgc caccgttcat ggttctgttg cttatgtttc acaagttcca   2100
tggataatga atggtactgt aaaggaaaac attttatttg ggcatagata cgacgcggaa   2160
ttttacgaaa aaacgatcaa ggcctgtgcg ttaactattg atcttgcaat tttgatggat   2220
ggagataaga cattagttgg cgagaaaggg atctccttat ctggaggaca aaaagctcgt   2280
ttgtctttag caagagcagt ttatgcgaga gctgacactt atttacttga tgatcctttg   2340
gcagctgttg atgaacacgt tgccaggcac ttgatcgaac atgtgttggg tccaaatggt   2400
ttattacata caaaaacgaa ggtattagcc actaataagg tgagcgcgtt atccatcgca   2460
gattctattg cattattaga taatggagaa atcacacagc agggtacata tgatgagatt   2520
acgaaggacg ctgattcgcc attatggaaa ttgctcaaca actatggtaa aaaaaataac   2580
ggtaagtcga atgaattcgg tgactcctct gaaagctcag ttcgagaaag tagtatacct   2640
gtagaaggag agctggaaca actgcagaaa ttaaatgatt tggattttgg caactctgac   2700
gccataagtt taaggagggc cagtgatgca actttgggaa gcatcgattt tggtgacgat   2760
gaaaatattg ctaaaagaga gcatcgtgaa cagggaaaag taaagtggaa catttaccta   2820
gagtacgcta aagcttgcaa cccgaaaagc gtttgtgtat tcatattgtt tattgttata   2880
tcgatgttcc tctctgttat gggtaacgtt tggttgaaac attggtctga agttaatagc   2940
cgctatggat ctaatccaaa tgccgcgcgt tacttggcca tttattttgc acttggtatt   3000
ggttcagcac tggcaacatt aatccagaca atcgttctct gggttttttg taccattcat   3060
gcctccaaat atttacacaa cttgatgaca aactctgtgt tgagagcccc aatgacgttt   3120
```

-continued

```
tttgaaacaa caccaatcgg tagaattcta aacagattct caaatgacat atacaaagtg    3180
gatgctttat taggaagaac attttctcag tttttcgtca atgcagtgaa agtcacattc    3240
actattacgg ttatctgtgc gacgacatgg caatttatct tcattatcat tccactaagt    3300
gtgttttaca tctactacca gcagtattac ctgagaacat caagggagtt gcgtcgttta    3360
gactctatta ctaggtctcc aatctactct catttccaag agactttggg tggccttgca    3420
acggttagag gttattctca acagaaaagg ttttcccaca ttaatcaatg ccgcattgat    3480
aataacatga gtgcgttcta tccctctatc aatgctaacc gttggctagc ataggttg      3540
gaacttattg gttcaattat cattctaggt gctgcaactt tatccgtttt tagactaaaa    3600
caaggcacat taacggcagg tatggtgggt ttatcattaa gctatgcttt acaaatcact    3660
caaacgttaa attggattgt tagaatgact gtggaagttg aaacgaatat tgtttcagtg    3720
gaaagaataa aggaatatgc tgatttgaag agcgaggcac ctttaatagt tgaaggccac    3780
agaccaccca agaatggcc gagccagggt gatataaagt ttaataatta ttccactcgt     3840
tataggccgg agcttgatct tgttctgaag cacattaata tacacattaa accaaatgaa    3900
aaagttggta tcgtgggtag aacgggtgcg ggaaaatcct cattaacgct agcattattc    3960
aggatgattg aggctagcga gggaaacatc gtaatcgaca acattgccat caacgagatt    4020
gggttatatg atttgagaca taaattgtca atcatacctc aggattctca agtttttgag    4080
ggcactgttc gtgagaacat tgatcccatt aaccaataca ctgatgaagc tatttggagg    4140
gcattggaac tttctcattt gaaagaacac gtgctatcaa tgagcaatga cggattagat    4200
gcccaactaa ccgaaggtgg tggcaactta agtgttggac aaagacaatt attatgtctt    4260
gcaagagcaa tgttggttcc atcaaagatt ttggtgcttg atgaagccac ggccgcagtc    4320
gacgtggaga cagataaagt cgtccaagag acgattcgta ctgctttcaa ggacagaact    4380
atcttgacca tcgcgcatag actgaacacg ataatggaca gtgatagaat catagtgttg    4440
gacaatggta aagtagccga gtttgactct ccgggccagt tattaagtga taacaaatca    4500
ttgttctatt cactgtgcat ggaggctggt ttggtcaatg aaaattaa                 4548
```

<210> SEQ ID NO 2
<211> LENGTH: 1515
<212> TYPE: PRT
<213> ORGANISM: Saccharomyces cerevisiae

<400> SEQUENCE: 2

```
Met Ala Gly Asn Leu Val Ser Trp Ala Cys Lys Leu Cys Arg Ser Pro
  1               5                  10                  15

Glu Gly Phe Gly Pro Ile Ser Phe Tyr Gly Asp Phe Thr Gln Cys Phe
             20                  25                  30

Ile Asp Gly Val Ile Leu Asn Leu Ser Ala Ile Phe Met Ile Thr Phe
         35                  40                  45

Gly Ile Arg Asp Leu Val Asn Leu Cys Lys Lys Lys His Ser Gly Ile
     50                  55                  60

Lys Tyr Arg Arg Asn Trp Ile Ile Val Ser Arg Met Ala Leu Val Leu
 65                  70                  75                  80

Leu Glu Ile Ala Phe Val Ser Leu Ala Ser Leu Asn Ile Ser Lys Glu
                 85                  90                  95

Glu Ala Glu Asn Phe Thr Ile Val Ser Gln Tyr Ala Ser Thr Met Leu
            100                 105                 110

Ser Leu Phe Val Ala Leu Ala Leu His Trp Ile Glu Tyr Asp Arg Ser
        115                 120                 125
```

-continued

```
Val Val Ala Asn Thr Val Leu Leu Phe Tyr Trp Leu Phe Glu Thr Phe
    130                 135                 140

Gly Asn Phe Ala Lys Leu Ile Asn Ile Leu Ile Arg His Thr Tyr Glu
145                 150                 155                 160

Gly Ile Trp Tyr Ser Gly Gln Thr Gly Phe Ile Leu Thr Leu Phe Gln
                165                 170                 175

Val Ile Thr Cys Ala Ser Ile Leu Leu Glu Ala Leu Pro Lys Lys
            180                 185                 190

Pro Leu Met Pro His Gln His Ile His Gln Thr Leu Thr Arg Arg Lys
        195                 200                 205

Pro Asn Pro Tyr Asp Ser Ala Asn Ile Phe Ser Arg Ile Thr Phe Ser
210                 215                 220

Trp Met Ser Gly Leu Met Lys Thr Gly Tyr Glu Lys Tyr Leu Val Glu
225                 230                 235                 240

Ala Asp Leu Tyr Lys Leu Pro Arg Asn Phe Ser Ser Glu Glu Leu Ser
                245                 250                 255

Gln Lys Leu Glu Lys Asn Trp Glu Asn Glu Leu Lys Gln Lys Ser Asn
            260                 265                 270

Pro Ser Leu Ser Trp Ala Ile Cys Arg Thr Phe Gly Ser Lys Met Leu
        275                 280                 285

Leu Ala Ala Phe Phe Lys Ala Ile His Asp Val Leu Ala Phe Thr Gln
290                 295                 300

Pro Gln Leu Leu Arg Ile Leu Ile Lys Phe Val Thr Asp Tyr Asn Ser
305                 310                 315                 320

Glu Arg Gln Asp Asp His Ser Ser Leu Gln Gly Phe Glu Asn Asn His
                325                 330                 335

Pro Gln Lys Leu Pro Ile Val Arg Gly Phe Leu Ile Ala Phe Ala Met
            340                 345                 350

Phe Leu Val Gly Phe Thr Gln Thr Ser Val Leu His Gln Tyr Phe Leu
        355                 360                 365

Asn Val Phe Asn Thr Gly Met Tyr Ile Lys Ser Ala Leu Thr Ala Leu
370                 375                 380

Ile Tyr Gln Lys Ser Leu Val Leu Ser Asn Glu Ala Ser Gly Leu Ser
385                 390                 395                 400

Ser Thr Gly Asp Ile Val Asn Leu Met Ser Val Asp Val Gln Lys Leu
                405                 410                 415

Gln Asp Leu Thr Gln Trp Leu Asn Leu Ile Trp Ser Gly Pro Phe Gln
            420                 425                 430

Ile Ile Ile Cys Leu Tyr Ser Leu Tyr Lys Leu Leu Gly Asn Ser Met
        435                 440                 445

Trp Val Gly Val Ile Ile Leu Val Ile Met Met Pro Leu Asn Ser Phe
450                 455                 460

Leu Met Arg Ile Gln Lys Lys Leu Gln Lys Ser Gln Met Lys Tyr Lys
465                 470                 475                 480

Asp Glu Arg Thr Arg Val Ile Ser Glu Ile Leu Asn Asn Ile Lys Ser
                485                 490                 495

Leu Lys Leu Tyr Ala Trp Glu Lys Pro Tyr Arg Glu Lys Leu Glu Glu
            500                 505                 510

Val Arg Asn Asn Lys Glu Leu Lys Asn Leu Thr Lys Leu Gly Cys Tyr
        515                 520                 525

Met Ala Val Thr Ser Phe Gln Phe Asn Ile Val Pro Phe Leu Val Ser
530                 535                 540
```

-continued

```
Cys Cys Thr Phe Ala Val Phe Val Tyr Thr Glu Asp Arg Ala Leu Thr
545                 550                 555                 560

Thr Asp Leu Val Phe Pro Ala Leu Thr Leu Phe Asn Leu Leu Ser Phe
                565                 570                 575

Pro Leu Met Ile Ile Pro Met Val Leu Asn Ser Phe Ile Glu Ala Ser
            580                 585                 590

Val Ser Ile Gly Arg Leu Phe Thr Phe Phe Thr Asn Glu Glu Leu Gln
        595                 600                 605

Pro Asp Ser Val Gln Arg Leu Pro Lys Val Lys Asn Ile Gly Asp Val
    610                 615                 620

Ala Ile Asn Ile Gly Asp Ala Thr Phe Leu Trp Gln Arg Lys Pro
625                 630                 635                 640

Glu Tyr Lys Val Ala Leu Lys Asn Ile Asn Phe Gln Ala Lys Lys Gly
                645                 650                 655

Asn Leu Thr Cys Ile Val Gly Lys Val Gly Ser Gly Lys Thr Ala Leu
                660                 665                 670

Leu Ser Cys Met Leu Gly Asp Leu Phe Arg Val Lys Gly Phe Ala Thr
            675                 680                 685

Val His Gly Ser Val Ala Tyr Val Ser Gln Val Pro Trp Ile Met Asn
690                 695                 700

Gly Thr Val Lys Glu Asn Ile Leu Phe Gly His Arg Tyr Asp Ala Glu
705                 710                 715                 720

Phe Tyr Glu Lys Thr Ile Lys Ala Cys Ala Leu Thr Ile Asp Leu Ala
                725                 730                 735

Ile Leu Met Asp Gly Asp Lys Thr Leu Val Gly Glu Lys Gly Ile Ser
            740                 745                 750

Leu Ser Gly Gly Gln Lys Ala Arg Leu Ser Leu Ala Arg Ala Val Tyr
        755                 760                 765

Ala Arg Ala Asp Thr Tyr Leu Leu Asp Asp Pro Leu Ala Ala Val Asp
    770                 775                 780

Glu His Val Ala Arg His Leu Ile Glu His Val Leu Gly Pro Asn Gly
785                 790                 795                 800

Leu Leu His Thr Lys Thr Lys Val Leu Ala Thr Asn Lys Val Ser Ala
                805                 810                 815

Leu Ser Ile Ala Asp Ser Ile Ala Leu Leu Asp Asn Gly Glu Ile Thr
                820                 825                 830

Gln Gln Gly Thr Tyr Asp Glu Ile Thr Lys Asp Ala Asp Ser Pro Leu
            835                 840                 845

Trp Lys Leu Leu Asn Asn Tyr Gly Lys Lys Asn Asn Gly Lys Ser Asn
        850                 855                 860

Glu Phe Gly Asp Ser Ser Glu Ser Ser Val Arg Glu Ser Ser Ile Pro
865                 870                 875                 880

Val Glu Gly Glu Leu Glu Gln Leu Gln Lys Leu Asn Asp Leu Asp Phe
                885                 890                 895

Gly Asn Ser Asp Ala Ile Ser Leu Arg Arg Ala Ser Asp Ala Thr Leu
                900                 905                 910

Gly Ser Ile Asp Phe Gly Asp Asp Glu Asn Ile Ala Lys Arg Glu His
            915                 920                 925

Arg Glu Gln Gly Lys Val Lys Trp Asn Ile Tyr Leu Glu Tyr Ala Lys
        930                 935                 940

Ala Cys Asn Pro Lys Ser Val Cys Val Phe Ile Leu Phe Ile Val Ile
945                 950                 955                 960

Ser Met Phe Leu Ser Val Met Gly Asn Val Trp Leu Lys His Trp Ser
```

-continued

```
                965                 970                 975
Glu Val Asn Ser Arg Tyr Gly Ser Asn Pro Asn Ala Ala Arg Tyr Leu
            980                 985                 990
Ala Ile Tyr Phe Ala Leu Gly Ile Gly Ser Ala Leu Ala Thr Leu Ile
            995                1000                1005
Gln Thr Ile Val Leu Trp Val Phe Cys Thr Ile His Ala Ser Lys Tyr
           1010                1015                1020
Leu His Asn Leu Met Thr Asn Ser Val Leu Arg Ala Pro Met Thr Phe
1025                1030                1035                1040
Phe Glu Thr Thr Pro Ile Gly Arg Ile Leu Asn Arg Phe Ser Asn Asp
                1045                1050                1055
Ile Tyr Lys Val Asp Ala Leu Leu Gly Arg Thr Phe Ser Gln Phe Phe
                1060                1065                1070
Val Asn Ala Val Lys Val Thr Phe Thr Ile Thr Val Ile Cys Ala Thr
                1075                1080                1085
Thr Trp Gln Phe Ile Phe Ile Ile Ile Pro Leu Ser Val Phe Tyr Ile
                1090                1095                1100
Tyr Tyr Gln Gln Tyr Tyr Leu Arg Thr Ser Arg Glu Leu Arg Arg Leu
1105                1110                1115                1120
Asp Ser Ile Thr Arg Ser Pro Ile Tyr Ser His Phe Gln Glu Thr Leu
                1125                1130                1135
Gly Gly Leu Ala Thr Val Arg Gly Tyr Ser Gln Gln Lys Arg Phe Ser
                1140                1145                1150
His Ile Asn Gln Cys Arg Ile Asp Asn Asn Met Ser Ala Phe Tyr Pro
            1155                1160                1165
Ser Ile Asn Ala Asn Arg Trp Leu Ala Tyr Arg Leu Glu Leu Ile Gly
            1170                1175                1180
Ser Ile Ile Leu Gly Ala Ala Thr Leu Ser Val Phe Arg Leu Lys
1185                1190                1195                1200
Gln Gly Thr Leu Thr Ala Gly Met Val Gly Leu Ser Leu Ser Tyr Ala
                1205                1210                1215
Leu Gln Ile Thr Gln Thr Leu Asn Trp Ile Val Arg Met Thr Val Glu
                1220                1225                1230
Val Glu Thr Asn Ile Val Ser Val Glu Arg Ile Lys Glu Tyr Ala Asp
                1235                1240                1245
Leu Lys Ser Glu Ala Pro Leu Ile Val Glu Gly His Arg Pro Pro Lys
                1250                1255                1260
Glu Trp Pro Ser Gln Gly Asp Ile Lys Phe Asn Asn Tyr Ser Thr Arg
1265                1270                1275                1280
Tyr Arg Pro Glu Leu Asp Leu Val Leu Lys His Ile Asn Ile His Ile
                1285                1290                1295
Lys Pro Asn Glu Lys Val Gly Ile Val Gly Arg Thr Gly Ala Gly Lys
            1300                1305                1310
Ser Ser Leu Thr Leu Ala Leu Phe Arg Met Ile Glu Ala Ser Glu Gly
            1315                1320                1325
Asn Ile Val Ile Asp Asn Ile Ala Ile Asn Glu Ile Gly Leu Tyr Asp
            1330                1335                1340
Leu Arg His Lys Leu Ser Ile Ile Pro Gln Asp Ser Gln Val Phe Glu
1345                1350                1355                1360
Gly Thr Val Arg Glu Asn Ile Asp Pro Ile Asn Gln Tyr Thr Asp Glu
                1365                1370                1375
Ala Ile Trp Arg Ala Leu Glu Leu Ser His Leu Lys Glu His Val Leu
                1380                1385                1390
```

```
Ser Met Ser Asn Asp Gly Leu Asp Ala Gln Leu Thr Glu Gly Gly Gly
        1395                1400                1405

Asn Leu Ser Val Gly Gln Arg Gln Leu Leu Cys Leu Ala Arg Ala Met
    1410                1415                1420

Leu Val Pro Ser Lys Ile Leu Val Leu Asp Glu Ala Thr Ala Ala Val
1425                1430                1435                1440

Asp Val Glu Thr Asp Lys Val Val Gln Glu Thr Ile Arg Thr Ala Phe
                1445                1450                1455

Lys Asp Arg Thr Ile Leu Thr Ile Ala His Arg Leu Asn Thr Ile Met
            1460                1465                1470

Asp Ser Asp Arg Ile Ile Val Leu Asp Asn Gly Lys Val Ala Glu Phe
        1475                1480                1485

Asp Ser Pro Gly Gln Leu Leu Ser Asp Asn Lys Ser Leu Phe Tyr Ser
    1490                1495                1500

Leu Cys Met Glu Ala Gly Leu Val Asn Glu Asn
1505                1510                1515

<210> SEQ ID NO 3
<211> LENGTH: 4776
<212> TYPE: DNA
<213> ORGANISM: Saccharomyces cerevisiae
<220> FEATURE:
<221> NAME/KEY: gene
<222> LOCATION: (0)...(0)
<223> OTHER INFORMATION: yhl035c gene

<400> SEQUENCE: 3
atgggaacgg atccccttat tatccgaaat aatggttcat tttgggaagt tgatgatttt        60
actcgtttag gaagaactca gctattgagc tactatttac cattggctat catagcctca       120
attggcattt tcgcactttg tcgcagtgga ttatctcgtt atgtaagatc tgccgagtgc       180
gatttagtga acgaatatct atttggcgca caagaagaga gaaagaagaa taatagtata       240
gaaagacttc tacggaactc aaatacccaa gccaattacg tcaacgtcaa aaagcaagga       300
aggattttga aacttagaca ttttgatata acaactatag atgtcaagca atcgatgct        360 aaaaatcatg gtggactaac gtttagtaga ccgtctacta gtgaccactt aagaaaatca       420
tctgaaattg tattaatgtc tttacaaata attggccttt ccttttaag agtaacaaaa        480 atcaatattg aattaacgaa cagagatgtt acaactttac tattattttg gttaatacta       540
ctttccctaa gtatcttaag agtttacaag cgttcaacga atctttgggc catctgtttt       600
actgcccata caactatttg gatttcaacc tggattccaa ttcgttcggt ctatattggt       660
aatatcgatg atgtacccct cacagatatt tacatctttg aattcgtaat tacttcaacc       720
ttacagccaa taaagctcac ttcaccgatt aaagacaact catccatcat ctacgttaga       780
gacgaccata cgtctccttc gagggaacac atatcctcaa ttttaagttg cattacttgg       840
agctggatta ccaattttat atgggaggcc caaagaaaca ctattaagtt aaaggatatt       900
tggggcttat caatggaaga ctatagcatt tcattctaa aagggtttac caggagaaac        960
aagcacatta taatttgac gctagcactg tttgaatctt tcaaaacata tttactcata       1020
ggaatgttat gggttctggt gaacagtatt gtaaaccttc ttcccacaat tttaatgaaa      1080
agatttttag aaattgtgga taacccaaac cgttcctcat catgcatgaa tttggcgtgg      1140
ctttatatta ttggtatgtt catttgtaga ttgacattag caatttgtaa ttcccaaggt      1200
caatttgttt ctgataagat tgtttaaga ataagagcca tactcatagg agaaatttat      1260
```

```
gcaaaaggct tacgtaggag gctgtttaca tctccaaaaa ccagctctga ttcagatagt    1320
atctccgcaa accttggtac cataattaat ctcatttcta ttgactcatt taaggtatcg    1380
gaactagcaa actacccttta tgtgacagtt caggcagtaa ttatgataat agttgttgta    1440
ggactacttt tcaactttttt aggtgtttca gcttttgcag gaatttcaat tatcttagtg    1500
atgttcccat tgaatttctt gttagcgaat ttgttaggta agtttcaaaa gcaaacactg    1560
aaatgtactg accaaagaat ctcaaaattg aacgagtgct tacagaacat aagaattgtc    1620
aaatattttg cttgggaaag gaatattata atgaaatca atcaataag gcaaaaggaa       1680 ttaagatcct tattaaaaaa atctttggtg tggtccgtaa cttctttttct ttggttcgtg    1740 acaccgacct tggtgacagg tgtcactttc gccatctgta catttgttca acatgaagat    1800
ttgaatgccc cgcttgcttt cactactttg tcactcttca ctttgttaaa gacacccctg    1860
gatcaattat caaatatgct aagtttcata atcaatcaa aagtctctct aaaaagaata     1920
agcgattttt taaggatgga cgatacagaa aaatataatc aactaaccat atctccagac    1980
aaaaataaaa ttgaatttaa aaatgcgact ttaacctgga atgaaaatga cagcgatatg    2040
aatgcattca aattatgtgg tttgaatatt aaatttcaaa ttggtaagtt aaatttgatt    2100
ttgggttcta caggatctgg taaaagtgca ttgctgctgg gtttactggg tgaactaaat    2160
ctaattagtg gctctatcat tgttccgagc ttagaaccaa agcatgattt aattcccgac    2220
tgcgaaggtt taaccaattc cttcgcatat tgttcacaaa gtgcgtggct attaaatgac    2280
acggtaaaaa acaatattat ctttgataac ttctataacg aggataggta caacaaagta    2340
attgatgcat gtgggctgaa aagagacctg gagatttttac cagcaggtga cctaacagaa    2400
attggtgaaa agggtataac tttatcagga gggcagaaac agagaatttc cttggcgaga    2460
gctgtttatt cgagtgctaa gcatgtctta ctagatgatt gtttgagcgc tgtcgattca    2520
catactgctg tatggatcta tgaaaattgc atcacaggtc cactaatgaa aaatagaacc    2580
tgcattttag ttacgcacaa tgtttcatta acacttagaa atgcccattt cgcgattgtg    2640
ttggaaaatg gcaaagtgaa gaatcaagga actattacag aattacaaag caaagggctt    2700
tttaaggaaa aatatgttca actttcttct cgagatagca ttaatgaaaa gaacgctaat    2760
agattaaaag ctcccagaaa aaatgactct cagaaaatcg aacctgtcac cgagaacata    2820
aattttgatg caaattttgt caatgatggc cagctaatag aagaggaaga aaaatcaaac    2880
ggtgccataa gccccgatgt ttataaatgg tacctgaaat ttttttggagg cttcaaagct    2940 ttaacagccc tgttcgctct ttatatcaca gctcaaattt tgttcatcag tcagtcttgg    3000
tggatacgac attgggtcaa cgataccaat gtacgaataa atgctccagg ttttgcgatg    3060
gacacgctgc cattaaaagg gatgaccgac tcttcgaaaa ataaacataa tgcatttttat    3120 tacttaaccg tatattttct tattggtatc attcaggcaa tgctaggtgg ttttaaaaca    3180
atgatgacgt ttttatccgg tatgcgagcc tccagaaaga tctttaataa tctgctagat    3240
ctagttctac atgcccaaat acgattttttc gacgtgacgc cggttggtag aatcatgaat    3300
cgcttttcaa aggacatcga aggtgttgat caagaattga ttccatactt agaagtaact    3360
atattttgcc taattcaatg cgcatcaatt atatttctca ttaccgtaat aactcctcgc    3420 tttttgcacag tcgccgttat cgttttttgtt ttatatttct ttgtgggaa atggtactta    3480 acggcaagta gagaattgaa aaggttagat tcaataacca aatcacccat ttttcaacat    3540
ttctcagaga ccttggtagg cgtttgcaca attcgtgcat ttggcgacga gaggagattc    3600
attttagaaa atatgaacaa aattgaccaa aataacagag cattcttttta tttatcagtt    3660
```

```
actgtcaaat ggttttcttt tagagtcgac atgattggcg cattcattgt tttagcatca    3720
ggttctttta ttctgctcaa tattgcaaat attgactcgg gtcttgccgg catttctttg    3780
acatatgcca ttttgttac agatggtgct ttatggttag ttagactgta ctcaacattt    3840
gaaatgaaca tgaactctgt tgaaagacta aaagaatatt ctagcattga acaagagaac    3900
tatcttggcc atgatgaagg ccgcattcta cttctaaacg aaccatcgtg gccaaaagat    3960
ggagaaattg aaattgaaaa cttatcttta cgttacgcgc caaatttgcc tcctgtcata    4020
agaaatgtta gtttcaaagt ggatcctcaa agtaagattg ggattgtcgg agaactggc    4080 gcaggcaaat ctaccataat aacggcatta ttcagattac tagaaccaat aaccggatgt    4140
atcaaaatag atgggcagga tataagtaaa attgatctcg ttacattacg tcgttccatt    4200
actatcatcc ctcaggaccc tattctattt gcaggtacaa tcaaaagtaa tgttgatcca    4260
tatgatgaat atgatgaaaa aaaaatattc aaagcacttt cacaagtaaa tctaatttct    4320
tcacatgaat ttgaagaagt gcttaactcg gaggaacgct ttaacagcac tcataataaa    4380
tttttaaatc ttcacacaga aatagctgag ggcggcttaa atctgtccca aggtgaaagg    4440
caattgcttt ttattgcacg atcattgtta cgcgagccaa agataatact tttggacgag    4500
gctacttcct ctattgatta cgattctgac catttaattc agggtattat aagaagtgag    4560
tttaataaaa gcacaattct tactattgca catcgtttga gatctgttat cgattacgac    4620
aggataattg tgatggatgc cggtgaggta aaagaatatg atcgccctag tgaactgttg    4680
aaagatgaac gcggtatatt ttatagtatg tgtcgtgaca gtgggggcct agagcttttg    4740
aagcaaatag ccaagcaatc aagtaagatg atgaaa                              4776
```

<210> SEQ ID NO 4
<211> LENGTH: 1592
<212> TYPE: PRT
<213> ORGANISM: Saccharomyces cerevisiae

<400> SEQUENCE: 4

```
Met Gly Thr Asp Pro Leu Ile Ile Arg Asn Asn Gly Ser Phe Trp Glu
  1               5                  10                  15

Val Asp Asp Phe Thr Arg Leu Gly Arg Thr Gln Leu Leu Ser Tyr Tyr
             20                  25                  30

Leu Pro Leu Ala Ile Ile Ala Ser Ile Gly Ile Phe Ala Leu Cys Arg
         35                  40                  45

Ser Gly Leu Ser Arg Tyr Val Arg Ser Ala Glu Cys Asp Leu Val Asn
     50                  55                  60

Glu Tyr Leu Phe Gly Ala Gln Glu Glu Arg Lys Glu Asp Asn Ser Ile
 65                  70                  75                  80

Glu Arg Leu Leu Arg Asn Ser Asn Thr Gln Ala Asn Tyr Val Asn Val
                 85                  90                  95

Lys Lys Gln Gly Arg Ile Leu Lys Leu Arg His Phe Asp Ile Thr Thr
            100                 105                 110

Ile Asp Val Lys Gln Ile Asp Ala Lys Asn His Gly Gly Leu Thr Phe
        115                 120                 125

Ser Arg Pro Ser Thr Ser Asp His Leu Arg Lys Ser Ser Glu Ile Val
    130                 135                 140

Leu Met Ser Leu Gln Ile Ile Gly Leu Ser Phe Leu Arg Val Thr Lys
145                 150                 155                 160

Ile Asn Ile Glu Leu Thr Asn Arg Asp Val Thr Thr Leu Leu Leu Phe
                165                 170                 175
```

-continued

Trp Leu Ile Leu Leu Ser Leu Ser Ile Leu Arg Val Tyr Lys Arg Ser
            180                 185                 190

Thr Asn Leu Trp Ala Ile Cys Phe Thr Ala His Thr Thr Ile Trp Ile
            195                 200                 205

Ser Thr Trp Ile Pro Ile Arg Ser Val Tyr Ile Gly Asn Ile Asp Asp
            210                 215                 220

Val Pro Ser Gln Ile Phe Tyr Ile Phe Glu Phe Val Ile Thr Ser Thr
225                 230                 235                 240

Leu Gln Pro Ile Lys Leu Thr Ser Pro Ile Lys Asp Asn Ser Ser Ile
                245                 250                 255

Ile Tyr Val Arg Asp Asp His Thr Ser Pro Ser Arg Glu His Ile Ser
            260                 265                 270

Ser Ile Leu Ser Cys Ile Thr Trp Ser Trp Ile Thr Asn Phe Ile Trp
            275                 280                 285

Glu Ala Gln Lys Asn Thr Ile Lys Leu Lys Asp Ile Trp Gly Leu Ser
290                 295                 300

Met Glu Asp Tyr Ser Ile Phe Ile Leu Lys Gly Phe Thr Arg Arg Asn
305                 310                 315                 320

Lys His Ile Asn Asn Leu Thr Leu Ala Leu Phe Glu Ser Phe Lys Thr
                325                 330                 335

Tyr Leu Leu Ile Gly Met Leu Trp Val Leu Val Asn Ser Ile Val Asn
            340                 345                 350

Leu Leu Pro Thr Ile Leu Met Lys Arg Phe Leu Glu Ile Val Asp Asn
            355                 360                 365

Pro Asn Arg Ser Ser Ser Cys Met Asn Leu Ala Trp Leu Tyr Ile Ile
            370                 375                 380

Gly Met Phe Ile Cys Arg Leu Thr Leu Ala Ile Cys Asn Ser Gln Gly
385                 390                 395                 400

Gln Phe Val Ser Asp Lys Ile Cys Leu Arg Ile Arg Ala Ile Leu Ile
                405                 410                 415

Gly Glu Ile Tyr Ala Lys Gly Leu Arg Arg Arg Leu Phe Thr Ser Pro
            420                 425                 430

Lys Thr Ser Ser Asp Ser Asp Ser Ile Ser Ala Asn Leu Gly Thr Ile
            435                 440                 445

Ile Asn Leu Ile Ser Ile Asp Ser Phe Lys Val Ser Glu Leu Ala Asn
            450                 455                 460

Tyr Leu Tyr Val Thr Val Gln Ala Val Ile Met Ile Ile Val Val Val
465                 470                 475                 480

Gly Leu Leu Phe Asn Phe Leu Gly Val Ser Ala Phe Ala Gly Ile Ser
                485                 490                 495

Ile Ile Leu Val Met Phe Pro Leu Asn Phe Leu Leu Ala Asn Leu Leu
            500                 505                 510

Gly Lys Phe Gln Lys Gln Thr Leu Lys Cys Thr Asp Gln Arg Ile Ser
            515                 520                 525

Lys Leu Asn Glu Cys Leu Gln Asn Ile Arg Ile Val Lys Tyr Phe Ala
            530                 535                 540

Trp Glu Arg Asn Ile Ile Asn Glu Ile Lys Ser Ile Arg Gln Lys Glu
545                 550                 555                 560

Leu Arg Ser Leu Leu Lys Lys Ser Leu Val Trp Ser Val Thr Ser Phe
                565                 570                 575

Leu Trp Phe Val Thr Pro Thr Leu Val Thr Gly Val Thr Phe Ala Ile
            580                 585                 590

-continued

```
Cys Thr Phe Val Gln His Glu Asp Leu Asn Ala Pro Leu Ala Phe Thr
        595                 600                 605

Thr Leu Ser Leu Phe Thr Leu Leu Lys Thr Pro Leu Asp Gln Leu Ser
        610                 615                 620

Asn Met Leu Ser Phe Ile Asn Gln Ser Lys Val Ser Leu Lys Arg Ile
625                 630                 635                 640

Ser Asp Phe Leu Arg Met Asp Asp Thr Glu Lys Tyr Asn Gln Leu Thr
                645                 650                 655

Ile Ser Pro Asp Lys Asn Lys Ile Glu Phe Lys Asn Ala Thr Leu Thr
            660                 665                 670

Trp Asn Glu Asn Asp Ser Asp Met Asn Ala Phe Lys Leu Cys Gly Leu
        675                 680                 685

Asn Ile Lys Phe Gln Ile Gly Lys Leu Asn Leu Ile Leu Gly Ser Thr
        690                 695                 700

Gly Ser Gly Lys Ser Ala Leu Leu Gly Leu Leu Gly Glu Leu Asn
705                 710                 715                 720

Leu Ile Ser Gly Ser Ile Ile Val Pro Ser Leu Glu Pro Lys His Asp
                725                 730                 735

Leu Ile Pro Asp Cys Glu Gly Leu Thr Asn Ser Phe Ala Tyr Cys Ser
            740                 745                 750

Gln Ser Ala Trp Leu Leu Asn Asp Thr Val Lys Asn Ile Ile Phe
        755                 760                 765

Asp Asn Phe Tyr Asn Glu Asp Arg Tyr Asn Lys Val Ile Asp Ala Cys
        770                 775                 780

Gly Leu Lys Arg Asp Leu Glu Ile Leu Pro Ala Gly Asp Leu Thr Glu
785                 790                 795                 800

Ile Gly Glu Lys Gly Ile Thr Leu Ser Gly Gly Gln Lys Gln Arg Ile
                805                 810                 815

Ser Leu Ala Arg Ala Val Tyr Ser Ser Ala Lys His Val Leu Leu Asp
            820                 825                 830

Asp Cys Leu Ser Ala Val Asp Ser His Thr Ala Val Trp Ile Tyr Glu
        835                 840                 845

Asn Cys Ile Thr Gly Pro Leu Met Lys Asn Arg Thr Cys Ile Leu Val
        850                 855                 860

Thr His Asn Val Ser Leu Thr Leu Arg Asn Ala His Phe Ala Ile Val
865                 870                 875                 880

Leu Glu Asn Gly Lys Val Lys Asn Gln Gly Thr Ile Thr Glu Leu Gln
                885                 890                 895

Ser Lys Gly Leu Phe Lys Glu Lys Tyr Val Gln Leu Ser Ser Arg Asp
            900                 905                 910

Ser Ile Asn Glu Lys Asn Ala Asn Arg Leu Lys Ala Pro Arg Lys Asn
        915                 920                 925

Asp Ser Gln Lys Ile Glu Pro Val Thr Glu Asn Ile Asn Phe Asp Ala
        930                 935                 940

Asn Phe Val Asn Asp Gly Gln Leu Ile Glu Glu Glu Lys Ser Asn
945                 950                 955                 960

Gly Ala Ile Ser Pro Asp Val Tyr Lys Trp Tyr Leu Lys Phe Phe Gly
                965                 970                 975

Gly Phe Lys Ala Leu Thr Ala Leu Phe Ala Leu Tyr Ile Thr Ala Gln
            980                 985                 990

Ile Leu Phe Ile Ser Gln Ser Trp Trp Ile Arg His Trp Val Asn Asp
        995                 1000                1005

Thr Asn Val Arg Ile Asn Ala Pro Gly Phe Ala Met Asp Thr Leu Pro
```

-continued

```
                  1010                1015                1020
Leu Lys Gly Met Thr Asp Ser Ser Lys Asn Lys His Asn Ala Phe Tyr
1025                1030                1035                1040

Tyr Leu Thr Val Tyr Phe Leu Ile Gly Ile Ile Gln Ala Met Leu Gly
                1045                1050                1055

Gly Phe Lys Thr Met Met Thr Phe Leu Ser Gly Met Arg Ala Ser Arg
                1060                1065                1070

Lys Ile Phe Asn Asn Leu Leu Asp Leu Val Leu His Ala Gln Ile Arg
            1075                1080                1085

Phe Phe Asp Val Thr Pro Val Gly Arg Ile Met Asn Arg Phe Ser Lys
1090                1095                1100

Asp Ile Glu Gly Val Asp Gln Glu Leu Ile Pro Tyr Leu Glu Val Thr
1105                1110                1115                1120

Ile Phe Cys Leu Ile Gln Cys Ala Ser Ile Ile Phe Leu Ile Thr Val
                1125                1130                1135

Ile Thr Pro Arg Phe Leu Thr Val Ala Val Ile Val Phe Val Leu Tyr
                1140                1145                1150

Phe Phe Val Gly Lys Trp Tyr Leu Thr Ala Ser Arg Glu Leu Lys Arg
            1155                1160                1165

Leu Asp Ser Ile Thr Lys Ser Pro Ile Phe Gln His Phe Ser Glu Thr
1170                1175                1180

Leu Val Gly Val Cys Thr Ile Arg Ala Phe Gly Asp Glu Arg Arg Phe
1185                1190                1195                1200

Ile Leu Glu Asn Met Asn Lys Ile Asp Gln Asn Asn Arg Ala Phe Phe
                1205                1210                1215

Tyr Leu Ser Val Thr Val Lys Trp Phe Ser Phe Arg Val Asp Met Ile
                1220                1225                1230

Gly Ala Phe Ile Val Leu Ala Ser Gly Ser Phe Ile Leu Leu Asn Ile
            1235                1240                1245

Ala Asn Ile Asp Ser Gly Leu Ala Gly Ile Ser Leu Thr Tyr Ala Ile
            1250                1255                1260

Leu Phe Thr Asp Gly Ala Leu Trp Leu Val Arg Leu Tyr Ser Thr Phe
1265                1270                1275                1280

Glu Met Asn Met Asn Ser Val Glu Arg Leu Lys Glu Tyr Ser Ser Ile
                1285                1290                1295

Glu Gln Glu Asn Tyr Leu Gly His Asp Glu Gly Arg Ile Leu Leu Leu
            1300                1305                1310

Asn Glu Pro Ser Trp Pro Lys Asp Gly Glu Ile Glu Ile Glu Asn Leu
            1315                1320                1325

Ser Leu Arg Tyr Ala Pro Asn Leu Pro Pro Val Ile Arg Asn Val Ser
1330                1335                1340

Phe Lys Val Asp Pro Gln Ser Lys Ile Gly Ile Val Gly Arg Thr Gly
1345                1350                1355                1360

Ala Gly Lys Ser Thr Ile Ile Thr Ala Leu Phe Arg Leu Leu Glu Pro
                1365                1370                1375

Ile Thr Gly Cys Ile Lys Ile Asp Gly Gln Asp Ile Ser Lys Ile Asp
                1380                1385                1390

Leu Val Thr Leu Arg Arg Ser Ile Thr Ile Ile Pro Gln Asp Pro Ile
            1395                1400                1405

Leu Phe Ala Gly Thr Ile Lys Ser Asn Val Asp Pro Tyr Asp Glu Tyr
            1410                1415                1420

Asp Glu Lys Lys Ile Phe Lys Ala Leu Ser Gln Val Asn Leu Ile Ser
1425                1430                1435                1440
```

```
Ser His Glu Phe Glu Glu Val Leu Asn Ser Glu Arg Phe Asn Ser
            1445                1450                1455

Thr His Asn Lys Phe Leu Asn Leu His Thr Glu Ile Ala Glu Gly Gly
        1460                1465                1470

Leu Asn Leu Ser Gln Gly Glu Arg Gln Leu Leu Phe Ile Ala Arg Ser
    1475                1480                1485

Leu Leu Arg Glu Pro Lys Ile Ile Leu Leu Asp Glu Ala Thr Ser Ser
        1490                1495                1500

Ile Asp Tyr Asp Ser Asp His Leu Ile Gln Gly Ile Ile Arg Ser Glu
1505                1510                1515                1520

Phe Asn Lys Ser Thr Ile Leu Thr Ile Ala His Arg Leu Arg Ser Val
            1525                1530                1535

Ile Asp Tyr Asp Arg Ile Ile Val Met Asp Ala Gly Glu Val Lys Glu
            1540                1545                1550

Tyr Asp Arg Pro Ser Glu Leu Leu Lys Asp Glu Arg Gly Ile Phe Tyr
            1555                1560                1565

Ser Met Cys Arg Asp Ser Gly Gly Leu Glu Leu Leu Lys Gln Ile Ala
    1570                1575                1580

Lys Gln Ser Ser Lys Met Met Lys
1585                1590

<210> SEQ ID NO 5
<211> LENGTH: 33
<212> TYPE: DNA
<213> ORGANISM: Artificial Sequence
<220> FEATURE:
<223> OTHER INFORMATION: YCFa primer

<400> SEQUENCE: 5
actaccgtaa agctcgagaa aatggctggt aat                           33

<210> SEQ ID NO 6
<211> LENGTH: 27
<212> TYPE: DNA
<213> ORGANISM: Artificial Sequence
<220> FEATURE:
<223> OTHER INFORMATION: YCFb primer

<400> SEQUENCE: 6
cttgcctaag tgacgtgacg tctcctt                                  27

<210> SEQ ID NO 7
<211> LENGTH: 24
<212> TYPE: DNA
<213> ORGANISM: Artificial Sequence
<220> FEATURE:
<223> OTHER INFORMATION: RT-YCF1A primer

<400> SEQUENCE: 7
catgagtgcg ttctatccct ctat                                     24

<210> SEQ ID NO 8
<211> LENGTH: 24
<212> TYPE: DNA
<213> ORGANISM: Artificial Sequence
<220> FEATURE:
<223> OTHER INFORMATION: RT-YCF1B primer

<400> SEQUENCE: 8
ccaccttcgg ttagttgggc atct                                     24
```

-continued

```
<210> SEQ ID NO 9
<211> LENGTH: 36
<212> TYPE: DNA
<213> ORGANISM: Artificial Sequence
<220> FEATURE:
<223> OTHER INFORMATION: forward primer: YHL035Ca

<400> SEQUENCE: 9
cgacgcggcc gcatgggaac ggatcccctt attatc                              36

<210> SEQ ID NO 10
<211> LENGTH: 35
<212> TYPE: DNA
<213> ORGANISM: Artificial Sequence
<220> FEATURE:
<223> OTHER INFORMATION: reverse primer: YHL035Cb

<400> SEQUENCE: 10
cgacgcggcc gccatcatct tacttgattg cttgg                               35
```